US007537892B2

(12) United States Patent
Hillis

(10) Patent No.: US 7,537,892 B2
(45) Date of Patent: *May 26, 2009

(54) METHOD AND SEQUENCES FOR DETERMINATE NUCLEIC ACID HYBRIDIZATION

(75) Inventor: William Daniel Hillis, Toluca Lake, CA (US)

(73) Assignee: Searete LLC, Bellevue, WA (US)

(*) Notice: Subject to any disclaimer, the term of this patent is extended or adjusted under 35 U.S.C. 154(b) by 27 days.

This patent is subject to a terminal disclaimer.

(21) Appl. No.: 11/205,583

(22) Filed: Aug. 16, 2005

(65) Prior Publication Data
US 2007/0042389 A1 Feb. 22, 2007

Related U.S. Application Data

(62) Division of application No. 09/821,694, filed on Mar. 28, 2001, now Pat. No. 6,949,340.

(51) Int. Cl.
*C12Q 1/68* (2006.01)
*C07H 21/04* (2006.01)

(52) U.S. Cl. .................. 435/6; 536/23.1; 536/24.3

(58) Field of Classification Search .................. None
See application file for complete search history.

(56) References Cited

U.S. PATENT DOCUMENTS

| | | | |
|---|---|---|---|
| 4,483,964 A | 11/1984 | Urdea et al. | |
| 4,517,338 A | 5/1985 | Urdea et al. | |
| 4,683,195 A | 7/1987 | Mullis et al. | |
| 4,683,202 A | 7/1987 | Mullis | |
| 4,786,600 A | 11/1988 | Kramer et al. | |
| 5,215,899 A | 6/1993 | Dattagupta | |
| 5,407,798 A | 4/1995 | Martinelli et al. | |
| 5,437,975 A | 8/1995 | McClelland et al. | |
| 5,492,806 A | 2/1996 | Drmanac et al. | |
| 5,503,980 A | 4/1996 | Cantor | |
| 5,508,169 A | 4/1996 | Deugau et al. | |
| 5,525,464 A | 6/1996 | Drmanac et al. | |
| 5,527,898 A | 6/1996 | Bauer et al. | |
| 5,552,278 A | 9/1996 | Brenner | |
| 5,578,443 A | 11/1996 | Santamaria et al. | |
| 5,695,940 A | 12/1997 | Drmanac et al. | |
| 5,728,532 A | 3/1998 | Ackley | |
| 5,744,305 A | 4/1998 | Fodor et al. | |
| 5,834,181 A | 11/1998 | Shuber | |
| 5,846,719 A | 12/1998 | Brenner et al. | |
| 5,858,731 A | 1/1999 | Sorge et al. | |
| 6,048,689 A * | 4/2000 | Murphy et al. ............ 435/6 |
| 6,051,380 A | 4/2000 | Sosnowski et al. | |
| 6,090,589 A | 7/2000 | Dimond et al. | |
| 6,297,006 B1 | 10/2001 | Drmanac et al. | |
| 6,461,871 B1 | 10/2002 | Kubista et al. | |
| 6,521,428 B1 | 2/2003 | Senapathy | |
| 6,949,340 B2 * | 9/2005 | Hilis ................. 435/6 |
| 2001/0029049 A1 | 10/2001 | Walt et al. | |
| 2004/0121319 A9 | 6/2004 | Hillis | |
| 2007/0042389 A1 * | 2/2007 | Hillis ................. 435/6 |

FOREIGN PATENT DOCUMENTS

| | | |
|---|---|---|
| WO | WO 94/01582 | 1/1994 |
| WO | WO 95/13369 | 5/1995 |
| WO | WO 95/20053 | 7/1995 |
| WO | WO 95/27080 | 10/1995 |
| WO | WO 99/22025 | 5/1999 |
| WO | WO 00/22171 | 4/2000 |
| WO | WO 02/079496 | 10/2002 |

OTHER PUBLICATIONS

Nampalli, Stayam et al. Efficient Synthesis of 8-oxo-dGTP: A mutagenic nucleotide. 2000. Bioorganic and Medicinal Chemistry Letters. vol. 10 pp. 1677-1679.*
Frieze et al.; "Optimal Reconstruction of a Sequence from its Probes;" *Journal of Computational Biology*; 1999; pp. 361-368; vol. 6, Nos. 3/4.
Preparata et al; "Sequencing-by-Hybridization at the Information-Theory Bound: An Optimal Algorithm;" *Journal of Computational Biology*; 2000; pp. 621-630; vol. 7, Nos. 3/4.
Alper, J.; "Drug Discovery on the Assembly Line" *Science* 264:1339-1401; Jun. 3, 1994.
Bains, W.; "Characterizing and sequencing cDNAs using oligonucleotide hybridization" *J.DNA Seuqencing and Mapping* 4:143-150; 1993.
Brenner, S.; "Encoded combinatorial chemistry" *Proc. Natl. Acad. Sci. USA* 89:5381-5383; Jun. 1992.
Brenner et al.; "Gene expression analysis by massively parallel signature sequencing (MPSS) on microbead arrays" *Nature Biotechnology* 18(6):630-634; Jun. 18, 2000.
Breslauer et al; "Predicting DNA duplex stability from the base sequence" *Proc. Natl. Acad. Sci. USA* 83:3746-3750; Jun. 1986.
Brown et al.; "Random mutagenesis of DNA using deoxynucleoside 5'-triphosphate analogues" *Amersham Life Science News* 23:18-19; 1997.

(Continued)

*Primary Examiner*—Carla Myers
*Assistant Examiner*—Amanda Shaw

(57) ABSTRACT

Provided are methods for using nucleic acid sequences having two or more degenerately pairing nucleotides, each degenerate nucleotide having a partially overlapping set of complementarity, to reduce the number of hybridizing nucleotide sequences or probes used in biochemical and molecular biological operations having sequence specific hybridization. The method may be employed for various hybridization procedures with sequence specific hybridization, including sequencing methods measuring hybridization directly, and tagging by hybridization methods in which the sequence is determined by analyzing the pattern of tags that hybridize thereto, and hybridization dependent amplification methods. The method involves hybridizing to the nucleic acid sequence of interest a first hybridizing nucleotide sequence and a second hybridizing nucleotide sequence, each comprising a sequence complementary, or complementary except at a position of interest or variable position, to a nucleic acid sequence of interest, and analyzing the whether some, all or none of the probes or tags hybridize.

14 Claims, 2 Drawing Sheets

OTHER PUBLICATIONS

Church et al.; "Multiplex DNA Sequencing" *Science* 240:185-188; Apr. 8, 1988.

Dollinger, G. "Nonbiological Applications" *The Polymerase Chain Reaction* Birkhauser, pp. 265-274; 1994.

Drmanac et al.; "DNA Sequence Determination by Hybridization: A Strategy for Efficient Large-Scale Sequencing" *Science* 260:1649-1652; Jun. 11, 1993.

Gyllensten et al.; "Generation of single-stranded DNA by the polymerase chain reaction and its application to direct sequencing of the *HLA-DQA* locus" *Proc. Natl. Acad. Sci. USA* 85:7652-7656; Oct. 1988.

Hill et al.; "Polymerase recognition of synthetic oligodeoxyribonucleotides incorporating degenerate pyrimidine and purine bases" *Proc. Natl. Acad. Sci. USA* 95:4258-4263; Apr. 1998.

Liang et al.; Differential Display of Eukaryotic Messenger RNA by Means of the Polymerase Chain Reaction; *Science* 257:967-971; 1992.

Maxam et al.; "A new method for sequencing DNA" *Proc. Natl. Acad. Sci. USA* 74(2):560-564; Feb. 1977.

Milligan et al.; "Current Concepts in Antisense Drug Design" *Journal of Medicinal Chemistry* 36(14):1923-1937.

Moriyama et al.; "synthesis and RNA polymerase incorporation of the degenerate ribonucleotide analogue rPTP" *Nucleic Acids Research* 26(9):2105-2111; May 1, 1998.

Needels et al.; "Generation and screening of an oligonucleotide-encoded synthetic peptide library" *Proc. Natl. Acad. Sci. USA* 90:10700-10704; Nov. 1993.

Pavlov et al.; "DNA Replication Fidelity with 8-Oxodeoxyguanosine Triphosphate" *Biochemistry* 33:4695-4701; Apr. 19, 1994.

Sanger et al.; "DNA sequencing with chain-terminating inhibitors" *Proc. Natl. Acad. Sci. USA* 74(12):5463-5467; Dec. 1977.

Schena et al.; "Quantitative Monitoring of Gene Expression Patterns with a Complementary DNA Microarray" *Science* 270:467-469; Oct. 20, 1995.

Unrau et al.; "Non-cloning amplification of specific DNA fragments from whole genomic DNA digests using DNA 'indexers'" *Gene* 145:163-169; 1994.

Velculescu et al.; "Serial Analysis of Gene Expression" *Science* 270:484-486; Oct. 20, 1995.

Vesnaver et al.; "The contribution of DNA single-stranded order to the thermodynamics of duplex formation" *Proc. Natl. Acad. Sci. USA* 88:3569-3573; May 1991.

Wallace et al.; "Hybridization of Synthetic oligodeoxyribonucleotides to $\Phi_x$ 174 RNA: the effect of single base pair mismatch" *Nucleic Acids Research* 6(11):3543-3557; Apr. 1979.

Wood et al.; "Base composition-independent hybridization in tetramethylammonium chloride: A method for oligonucleotide screening of highly complex gene libraries" *Proc. Natl. Acad. Sci. USA* 82:1585-1588; Mar. 1985.

Zaccolo et al.; "An Approach to Random Mutagenesis of DNA Using Mixtures of Triphosphate Derivatives of Nucleoside Analogues" *J. Mol. Biol.* 255(4):589-603; Feb. 2, 1996.

Brown, Betty A.; Kilpatrick, David R.; Oberste, M. Steven; Pallansch, Mark A.; "Serotype-specific identification of enterovirus 71 by PCR"; Journal of Clinical Virology; 2000; pp. 107-112; vol. 16; Elsevier.

De, Lina; Yang, Chen-Fu; Silva, Edson Da; Boshell, Jorge; Cáceres, Patricia; Gómez, Juan Ruiz; Pallansch, Mark; Kew, Olen; "Genotype-Specific RNA Probes for Direct Identification of Wild Polioviruses by Blot Hybridization"; Journal of Clinical Microbiology; Nov. 1997; pp. 2834-2840; vol. 35, No. 11; American Society for Microbiology.

De, Lina; Nottay, Baldev; Yang, Chen-Fu; Holloway, Brian P.; Pallansch, Mark; Kew, Olen; "Identification of Vaccine-Related Polioviruses by Hybridization with Specific RNA Probes"; Journal of Clinical Microbiology; Mar. 1995; pp. 562-571; vol. 33, No. 3.

Kilpatrick, David R.; Nottay Baldev; Yang, Chen-Fu; Yang, Su-Ju; Mulders, Mick N.; Holloway, Brian P.; Pallansch, Mark A.; Kew, Olen M.; "Group-Specific Identification of Polioviruses by PCR Using Primers Containing Mixed-Base or Deoxyinosine Residues at Positions of Codon Degeneracy"; Journal of Clinical Microbiology; Dec. 1996; pp. 2990-2996; vol. 34, No. 12; American Society for Microbiology.

Kilpatrick, David R.; Quay, Jacqueline; Pallansch, Mark A.; Oberste, M. Steven; "Type-Specific Detection of Echovirus 30 Isolates Using Degenerate Reverse Transcriptase PCR Primers"; Journal of Clinical Microbiology; Apr. 2001; pp. 1299-1302; vol. 39, No. 4.

Kilpatrick, David R.; Nottay Baldev; Yang, Chen-Fu; Yang, Su-Ju; Silva, Edson Da; Peñaranda, Silvia; Pallansch, Mark; Kew, Olen; "Serotype-Specific Identification of Polioviruses by PCR Using Primers Containing Mixed-Based or Deoxyinosine Residues at Positions of Codon Degeneracy"; Journal of Clinical Microbiology; Feb. 1998; pp. 352-357; vol. 36, No. 2; American Society for Microbiology.

Bonitz, Susan G.; Berlani, Roberta; Coruzzi, Gloria; Li, May; Macino, Guiseppe; Nobrega, Francisco G.; Nobrega, Marina P.; Thalenfeld, Barbara E.; and Tzagoloff, Alexander; "Codon recognition rules in yeast mitochondria"; Proceedings of the National Academy of Sciences, Biochemistry; bearing a date of Jun. 1980; pp. 3167-3170; vol. 77, No. 6.

Crick, F.H.C.; "Codon—Anticodon Pairing: The Wobble Hypothesis"; Journal of Molecular Biology; bearing a date of 1966; pp. 548-555; vol. 19.

Findley, G.L.; Findley, A.M.; and McGlynn, S.P.; "Symmetry characteristics of the genetic code"; Proceedings of the National Academy of. Sciences, Mathematics; bearing a date of Nov. 1982; pp. 7061-7065; vol. 79.

Igo, Robert P. Jr.; Lawson, Sobomabo D.; and Stuart, Kenneth; "RNA Sequence and Base Pairing Effects on Insertion Editing in *Trypanosoma brucei*"; Molecular and Cellular Biology; bearing a date of Mar. 2002; pp. 1567-1576; vol. 22, No. 5; American Society for Microbiology.

* cited by examiner

P-imino-A

P-amino-G

A-B-oxo-G

C-B-oxo-G

SEQUENCE LISTING

<160> NUMBER OF SEQ ID NOS: 50

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Analyte -continued sequence

<400> SEQUENCE: 1
ataaagctgc ttc                                                              13

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Labeling
      structure

<400> SEQUENCE: 2
aaaaaaaaac cccctttcct ttt                                                   23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Labeling
      structure

<400> SEQUENCE: 3
aaaaaaaaac ccccttttt ttt                                                    23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Labeling
      structure

<400> SEQUENCE: 4
aaaagaaaac cccctttct ttt                                                    23

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Adaptor
      sequence

<400> SEQUENCE: 5
acgagctgcc agtc                                                             14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Adaptor
      sequence

<400> SEQUENCE: 6
gactggcagc tcga                                                             14

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence

```
<220> FEATURE:
<221> NAME/KEY: modified_base
<222> LOCATION: (1)..(3)
<223> OTHER INFORMATION: a, t, g, or c
<220> FEATURE:
<221> NAME/KEY: modified_base
<222> LOCATION: (4)
<223> OTHER INFORMATION: synthetic c or t nucleotide

<400> SEQUENCE: 7
nnnnacgagc tgccagtcca tttaggcg                                         28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)..(3)
<223> OTHER INFORMATION: a, t, g, or c
<220> FEATURE:
<221> NAME/KEY: modified_base
<222> LOCATION: (4)
<223> OTHER INFORMATION: 8-oxo-dG

<400> SEQUENCE: 8
nnngacgagc tgccagtccg ctttgtag                                         28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)..(2)
<223> OTHER INFORMATION: a, t, g, or c
<220> FEATURE:
<221> NAME/KEY: modified_base
<222> LOCATION: (3)
<223> OTHER INFORMATION: synthetic c or t nucleotide
<220> FEATURE:
<221> NAME/KEY: modified_base
<222> LOCATION: (4)
<223> OTHER INFORMATION: a, t, g, or c

<400> SEQUENCE: 9
nnnnacgagc tgccagtcgg aacctgaa                                         28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)..(2)
<223> OTHER INFORMATION: a, t, g, or c
<220> FEATURE:
<221> NAME/KEY: modified_base
<222> LOCATION: (3)
<223> OTHER INFORMATION: 8-oxo-dG
<220> FEATURE:
<221> NAME/KEY: modified_base
<222> LOCATION: (4)
<223> OTHER INFORMATION: a, t, g or c
```

<400> SEQUENCE: 10
nngnacgagc tgccagtcat tcctcctc                                           28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)
<223> OTHER INFORMATION: a, t, g, or c
<220> FEATURE:
<221> NAME/KEY: modified_base
<222> LOCATION: (2)
<223> OTHER INFORMATION: synthetic c or t nucleotide
<220> FEATURE:
<221> NAME/KEY: modified_base
<222> LOCATION: (3)..(4)
<223> OTHER INFORMATION: a, t, g, or c

<400> SEQUENCE: 11
nnnnacgagc tgccagtccg aagaagtc                                           28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)
<223> OTHER INFORMATION: a, t, g, or c
<220> FEATURE:
<221> NAME/KEY: modified_base
<222> LOCATION: (2)
<223> OTHER INFORMATION: 8-oxo-dG
<220> FEATURE:
<221> NAME/KEY: modified_base
<222> LOCATION: (3)..(4)
<223> OTHER INFORMATION: a, t, g, or c

<400> SEQUENCE: 12
ngnnacgagc tgccagtcgg cgataact                                           28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)
<223> OTHER INFORMATION: synthetic c or t nucleotide
<220> FEATURE:
<221> NAME/KEY: modified_base
<222> LOCATION: (2)..(4)
<223> OTHER INFORMATION: a, t, g, or c

<400> SEQUENCE: 13
nnnnacgagc tgccagtcgc atccatct                                           28

<210> SEQ ID NO 14
<211> LENGTH: 28

```
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)
<223> OTHER INFORMATION: 8-oxo-dG
<220> FEATURE:
<221> NAME/KEY: modified_base
<222> LOCATION: (2)..(4)
<223> OTHER INFORMATION: a, t, g, or c

<400> SEQUENCE: 14
gnnnacgagc tgccagtcgc cagtgtta                                          28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)..(3)
<223> OTHER INFORMATION: a, t, g, or c

<400> SEQUENCE: 15
nnnyacgagc tgccagtcca tttaggcg                                          28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)..(3)
<223> OTHER INFORMATION: a, t, g, or c

<400> SEQUENCE: 16
nnnkacgagc tgccagtccg ctttgtag                                          28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)..(2)
<223> OTHER INFORMATION: a, t, g, or c
<220> FEATURE:
<221> NAME/KEY: modified_base
<222> LOCATION: (4)
<223> OTHER INFORMATION: a, t, g, or c

<400> SEQUENCE: 17
nnynacgagc tgccagtcgg aacctgaa                                          28

<210> SEQ ID NO 18
<211> LENGTH: 28
<212> TYPE: DNA
<213> ORGANISM: Artificial Sequence
<220> FEATURE:
```

<223> OTHER INFORMATION: Description of Artificial Sequence: Adaptor
      sequence
<220> FEATURE:
<221> NAME/KEY: modified_base
<222> LOCATION: (1)..(2)
<223> OTHER INFORMATION: a, t, g, or c
<220> FEATURE:
<221> NAME/KEY: modified_base
<222> LOCATION: (4)
<223> OTHER INFORMATION: a, t, g, or c

<400> SEQUENCE: 18
nnknacgagc tgccagtcat tcctcctc                                          28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)
<223> OTHER INFORMATION: a, t, g, or c
<220> FEATURE:
<221> NAME/KEY: modified_base
<222> LOCATION: (3)..(4)
<223> OTHER INFORMATION: a, t, g, or c

<400> SEQUENCE: 19
nynnacgagc tgccagtccg aagaagtc                                          28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (1)
<223> OTHER INFORMATION: a, t, g, or c
<220> FEATURE:
<221> NAME/KEY: modified_base
<222> LOCATION: (3)..(4)
<223> OTHER INFORMATION: a, t, g, or c

<400> SEQUENCE: 20
nknnacgagc tgccagtcgg cgataact                                          28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Adaptor
      sequence
<220> FEATURE:
<221> NAME/KEY: modified_base
<222> LOCATION: (2)..(4)
<223> OTHER INFORMATION: a, t, g, or c

<400> SEQUENCE: 21
ynnnacgagc tgccagtcgc atccatct                                          28

<210> SEQ ID NO 22
<211> LENGTH: 28
<212> TYPE: DNA
<213> ORGANISM: Artificial Sequence

```
<220> FEATURE:
<223> OTHER INFORMATION: Description of Artificial Sequence: Adaptor
      sequence
<220> FEATURE:
<221> NAME/KEY: modified_base
<222> LOCATION: (2)..(4)
<223> OTHER INFORMATION: a, t, g, or c

<400> SEQUENCE: 22
knnnacgagc tgccagtcgc cagtgtta                                         28

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 23
catttaggcg                                                             10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 24
ggaacctgaa                                                             10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 25
cgaagaagtc                                                             10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 26
gcatccatct                                                             10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 27
cgcctaaatg                                                             10

<210> SEQ ID NO 28
```

```
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 28
ttcaggttcc                                                           10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 29
gacttcttcg                                                           10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 30
agatggatgc                                                           10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 31
cgctttgtag                                                           10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 32
attcctcctc                                                           10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 33
ggcgataact                                                           10

<210> SEQ ID NO 34
<211> LENGTH: 10
```

```
<212> TYPE: DNA
<213> ORGANISM: Artificial Sequence
<220> FEATURE:
<223> OTHER INFORMATION: Description of Artificial Sequence: Decoder
      binding sequence

<400> SEQUENCE: 34
gccagtgtta                                                          10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 35
ctacaaagcg                                                          10

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 36
gaggaggaat                                                          10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 37
agttatcgcc                                                          10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Decoder
      probe sequence

<400> SEQUENCE: 38
taacactggc                                                          10

<210> SEQ ID NO 39
<211> LENGTH: 21
<212> TYPE: DNA
<213> ORGANISM: Homo sapiens

<400> SEQUENCE: 39
tttgtgaatg aggccgcata t                                             21

<210> SEQ ID NO 40
<211> LENGTH: 21
<212> TYPE: DNA
<213> ORGANISM: Homo sapiens

<400> SEQUENCE: 40
```

```
atatgcggcc tcattcacaa a                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 41
atatgcggcc bcattcacaa a                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (11)
<223> OTHER INFORMATION: synthetic c or t nucletoide

<400> SEQUENCE: 42
atatgcggcc ncattcacaa a                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (11)
<223> OTHER INFORMATION: 8-oxo-dG

<400> SEQUENCE: 43
atatgcggcc gcattcacaa a                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 44
atatgcggcc ycattcacaa a                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
atatgcggcc kcattcacaa a                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 46
atatgcggcc ccattcacaa a                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 47
atatgcggcc gcattcacaa a                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 48
atatgcggcc rcattcacaa a                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 49
atatgcggcc scattcacaa a                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Probe for
      the ORF 854 mutation

<400> SEQUENCE: 50
atatgcggcc acattcacaa a                                              21
```

METHOD AND SEQUENCES FOR DETERMINATE NUCLEIC ACID HYBRIDIZATION

This application is a divisional of and claims benefit of U.S. patent application Ser. No. 09/821,694, filed Mar. 28, 2001, titled METHODS AND SEQUENCES FOR DETERMINATE NUCLEIC ACID HYBRIDIZATION, U.S. Pat. No. 6,949,340, issued Sep. 27, 2005.

FIELD OF THE INVENTION

The present invention is directed to a method and nucleic acid sequences for determinate hybridization of nucleic acid analytes using hybridization probe sets.

BACKGROUND OF THE INVENTION

The ability to detect specific target nucleic acid analytes using nucleic acid probe hybridization and nucleic acid amplification methods has many applications. These applications include: nucleic acid sequencing, diagnoses of infectious or genetic diseases or cancers in humans or other animals; identification of viral or microbial contamination in cosmetics, foods, pharmaceuticals or water; and identification or characterization of, or genetic discrimination between individuals, for diagnosis of disease and genetic predisposition to disease, forensic or paternity testing and genetic analyses, for example breeding or engineering stock improvements in plants and animals.

The basis of nucleic acid probe hybridization methods and applications is the specific hybridization of an oligonucleotide or a nucleic acid fragment probe to form a stable, double-stranded hybrid through complementary base-pairing to particular nucleic acid sequence segments in an analyte molecule. Particular nucleic acid sequences may occur in only cells from a species, strain, individual or organism. Sequence specific hybridization of oligonucleotides and their analogs is a fundamental biotechnological process employed in various research, medical, and industrial applications. Specific hybridization by base pairing complementarity is utilized, for example, in identification of disease-related polynucleotides in diagnostic assays, screening of clones for polynucleotides containing a sequence of interest, identification of specific polynucleotides in mixtures of polynucleotides, amplification of specific target polynucleotides by, for example, polymerase chain reaction (PCR) and replicase enzyme mediated techniques, hybridization based histologic tissue staining, as in in situ PCR staining for histopathology, therapeutic blocking of expressed mRNA by anti-sense sequences, and DNA sequencing. For descriptions of these and other methods see for example, Sambrook et al. (1989) *Molecular Cloning. A Laboratory Manual*, 2$^{nd}$ Edition, Cold Spring Harbor Laboratory, New York; Keller and Manak, *DNA Probes* (1993)2$^{nd}$ Edition, Stockton Press, New York; Milligan et al. (1993) *J. Med. Chem.* 36:1923-1937; Drmanac et al. (1993) *Science* 260:1649-52; Bains (1993) *J. DNA Sequencing and Mapping* 4: 143-50; U.S. Pat. Nos. 4,683,195 and 4,683,202 to Mullis et al; and U.S. Pat. Nos. 4,483,964 and 4,517,338 to Urdea et al.

Base pairing specific hybridization has been proposed as a method of tracking, retrieving, and identifying compounds labeled with oligonucleotide tags. For example, in multiplex DNA sequencing, oligonucleotide tags are used to identify electrophoretically separated bands on a gel that consist of DNA fragments generated in the same sequencing reaction. DNA fragments from multiple sequencing reactions are thus separated on the same lane of a gel that is then blotted with separate solid phase materials on which the fragment bands from individual sequencing reactions are separately visualized by use of oligonucleotide probes that hybridize to complementary tags specific to the individual reaction (Church et al. (1988) *Science* 240: 185-88). Other uses of oligonucleotide tags or labels identifiable by hybridization based amplification have been proposed for identifying explosives, potential pollutants, such as crude oil, and currency for prevention and detection of counterfeiting. Dollinger reviews these methods, pages 265-274, in Mullis et al., Ed. (1994) *The Polymerase Chain Reaction* Birkhauser, Boston. More recently, systems employing oligonucleotide tags have also been proposed as a means of labeling, manipulating and identifying individual molecules in complex combinatorial chemical libraries, for example, as an aid to screening such libraries for drug candidates, Brenner and Lerner (1992) *Proc. Natl. Acad. Sci.* 89:5381-83; Alper (1994) *Science* 264: 1399-1401; and Needels et al. (1993) *Proc. Natl. Acad. Sci.* 90: 10700-704.

Recombinant DNA technology has permitted amplification and isolation of short fragments of genomic DNA (from 200 to 500 bp) to obtain a sufficient quantity of material for determination of the nucleotide sequence from a cloned fragment. The sequence is then determined.

Distinguishing among the four nucleotides was historically achieved in two ways: (1) by specific chemical degradation of the DNA fragment at specific nucleotides, in accordance with the Maxam and Gilbert method (Maxam, A. M. and Gilbert, W. (1977) *Proc. Natl. Acad. Sci.* 74:560); or (2) utilizing the dideoxy sequencing method described by Sanger (Sanger, F., et al. (1977) *Proc. Natl. Acad. Sci.* 74:5463). The dideoxy sequencing method of Sanger results in termination of polymerization at polymer sequence positions that incorporate the specific dideoxy base instead of the corresponding deoxy base, a probabilistic event, which generates sequence segments of different length. The length of these dideoxy terminated sequence segments is determined by separation on polyacrylamide gels that separate DNA fragments in the range of 1 to 500 bp, differing in length by one nucleotide or more. The length of the terminated nucleotide sequence segments for a reaction employing the dideoxy analog of a given base indicates the positions in the sequence of interest occupied by that base.

Both preceding methods are laborious, with competent laboratories able to sequence approximately 100 bp per person per day. With the use of computers and robotics, sequencing can be accelerated by several orders of magnitude.

Sequencing the entire human genome has been widely discussed. Generally appreciated is that such is possible only in large organized centers at a cost on the order of billions of dollars, and would require at least ten years. For accuracy, three lengths of a genome must be sequenced, because of random formation of cloned fragments of about 500 bp. 10 billion bp could be sequenced in approximately 30 years in a center sequencing about a million base pairs per day. Ten such centers would be required to sequence the entire human genome in several years.

A desire for understanding the genetic basis of disease and a host of other physiological states associated with different gene expression patterns has motivated the development of several approaches to large-scale DNA analysis (Adams et al., Ed. (1994) *Adams DNA Sequencing and Analysis*, Academic Press, New York). Contemporary analysis techniques for patterns of gene expression include large-scale sequencing, differential display, indexing schemes, subtraction hybridization, hybridization with solid phase arrays of cDNAs or oligonucleotides, and numerous DNA fingerprinting techniques. See, e.g., Lingo et al. (1992) *Science* 257:967-71; Erlander et al. PCT Pat. App. No. PCT/US94/13041; McClelland et al, U.S. Pat. No. 5,437,975; Unrau et al. *Gene* (1994) 145:163-69; Schena et al. (1995) *Science* 270: 467-469; Velculescu et al. (1995) *Science* 270:484-86.

These methods may be grouped into sequencing by direct analysis of hybridization data per se, and methods that label or tag a sequence segment by hybridization. One important subclass of the tag or label group of techniques employs double stranded oligonucleotide adaptors to classify populations of polynucleotides and/or to identify nucleotides at the termini of polynucleotides, e.g. Unrau et al (1994) supra and U.S. Pat. No. 5,508,169; Sibson, PCT Pat. App. Nos. PCT/GB93/01452 and PCT/GB95/00109; Cantor, U.S. Pat. No. 5,503,980; and Brenner, PCT Pat. App. No. PCT/US95/03678 and U.S. Pat. No. 5,552,278. Adapters employed in the preceding techniques typically have protruding single strands that permit specific hybridization and ligation to polynucleotides having complementary single stranded ends ("sticky overhangs"). Identification or classification may be effected by carrying out the reactions in separate vessels, or by providing secondary labels which identify one or more nucleotides in the protruding strand of the ligated adaptor, for example by hybridization.

Successful implementation of such tagging schemes depends in large part on the success in achieving specific hybridization between analyte sequence and the adaptor-tag, and between a tag or primary probe and its complementary or secondary probe.

In techniques employing base pairing specific nucleic acid hybridization in general, including sequencing by hybridizing tags or labels, for an oligonucleotide tag to successfully identify a substance, the number of false positive and false negative signals must be minimized. Unfortunately, such spurious signals are not uncommon because base pairing and stacking free energies vary widely among nucleotides in a duplex or triplex hybridized structure. Duplexes consisting of a repeated sequence of deoxyadenosine (A) and deoxythymidine (T) (or the RNA analogs, adenosine and thymidine) bound to its complementary nucleic acid sequence, are typically less stable than an equal-length duplex consisting of a repeated sequence of deoxyguanosine (G) and deoxycytidine (C) bound to a complementary or even partially complementary target containing a mismatch. The preceding is widely appreciated, explaining the higher melting temperature ($T_m$) of GC rich double stranded (DS) sequences compared to DS AT rich sequences. Thus, if a desired compound from a large combinatorial chemical library were tagged with the former oligonucleotide, a significant possibility would exist that under hybridization conditions designed to detect perfectly matched AT-rich duplexes, undesired compounds labeled with the GC-rich oligonucleotide—even in a mismatched duplex—would be detected along with the perfectly matched duplexes consisting of the AT-rich tag.

In the molecular tagging system proposed by Brenner et al. supra, the related problem of mis-hybridizations of closely related (i.e. Sequentially homologous) tags was addressed by employing a so-called "comma-less" code, which ensures that a probe out of register (or frame shifted) with respect to its complementary tag would result in a duplex with one or more mismatches for each of its five or more three-base words, or "codons." Although reagents, such as tetramethylammonium chloride, are available to negate base-specific stability differences of oligonucleotide duplexes, their effect is often limited and their presence may be incompatible with, or may practically complicate, further manipulations of the hybridized complexes, e.g. amplification by polymerase chain reaction (PCR), or the like.

Analogous problems have unduly complicated the simultaneous use of multiple hybridization probes, for example in analysis of multiple or complex genetic loci, e.g. via multiplex PCR, reverse dot blotting, or the like, or simply in "two-color" hybridization. Therefore, direct sequencing of certain loci, e.g. HLA genes, is advocated as a reliable alternative to indirect methods employing specific hybridization for the identification of genotypes, see, e.g., Gyllensten et al. (1988) *Proc. Natl. Acad. Sci.* 85:7652-56.

There remains a need in the art for methods for systematically employing a smaller number of hybridizing nucleic acid sequences, while obtaining the same amount of information from the hybridization. There also remains a need to reduce the differences in base pairing energies, especially at sequence positions of interest between different pairs of complementary nucleotide bases.

When hybridization based sequencing, regardless of the specific type is the assay at hand, a larger number of hybridizing probes is required than in processes that employ hybridization for detection by amplification such as PCR based methods.

There remains a need for a method for streamlining the number of probes and experiments required for processes that involve hybridization, and especially for sequencing by hybridization methods, while maintaining these processes as determinate or sequence specific.

SUMMARY OF THE INVENTION

A method is provided for using nucleic acid sequences or sets of sequences having one or more degenerately pairing nucleotide sequence positions, these positions corresponding to a probed or variable position or position of interest, either by use of a degenerately pairing nucleotide or by use of two different nucleotides at the position, wherein each degenerate nucleotide position has a partially overlapping set of complementarity to reduce the number of hybridizing nucleotide sequences or probes used in biochemical and molecular biological operations employing sequence specific hybridization. The method may be employed for various hybridization procedures in which sequence specific hybridization occurs, including sequencing methods that measure hybridization directly, as by array based methods that analyze hybridization patterns and by tagging by hybridization methods in which the sequence is determined by the tagged nucleic acid sequences that hybridize thereto. The invention may also be employed in conjunction with hybridization dependent amplification methods.

The invention provides a method of reducing the required number of unique hybridizing sequences that may be used to hybridize to a nucleic acid sequence of interest under hybridizing conditions. The method involves hybridizing to the nucleic acid sequence of interest a first hybridizing nucleotide sequence and a second hybridizing nucleotide sequence, each hybridizing nucleotide sequence comprising a sequence segment complementary to a nucleic acid sequence of interest, or complementary to a nucleic acid sequence of interest except at a position of interest or probed position which comprises the position pairing to a degenerately pairing nucleotide. Additional probes or hybridizing nucleotide sequences are required if there are more than four nucleotides that may be present at the variable position or position of interest. For four possible nucleotides in a sequence, two nucleic acid hybridizing sequences are required each having a nucleotide base pairing to a set of two nucleotides at the variable position, the two sets overlapping in one nucleotide, which is common to both sets.

The position of the first hybridizing nucleotide sequence probe corresponding to the variable or probed position comprises a nucleotide base pairing with a first set of two or more nucleotides, and the position of the second hybridizing nucleotide corresponding to the variable position comprises a nucleotide base pairing with a second set of two or more nucleotides. The first set of two or more nucleotides present in the analyte nucleic acid sequence includes at least one nucleotide that is a member of the second set of two or more nucleotides present in the nucleic acid sequence. The base pairing sets comprising the first set of two or more nucleotides and the second set of two or more nucleotides are not identical. A nucleotide present in the nucleic acid sequence of interest is not represented in the first base pairing set of two or more nucleotides, and the same nucleotide not represented in the first set of two or more nucleotides is also not present in the second base pairing set of two or more nucleotides. The conditions are such that hybridization of each of the first and second hybridizing nucleotide sequences occurs only if complementarity exists between a nucleotide at the variable position of the sequence of interest and a nucleotide at the corresponding position of these hybridizing nucleotide sequences.

Depending upon the identity of the nucleotide at the variable position of the sequence of interest, one both or neither of the first hybridizing nucleotide sequence and the second hybridizing nucleotide sequence hybridize to the sequence of interest. The probes or hybridizing sequences having a multiply base pairing nucleotide may be simultaneously, sequentially or separately hybridized to the nucleic acid sequence of interest, to which they are to be hybridized.

Provided for the determinate use of degenerately complementary nucleotides having overlapping base pairing complementarity sets, are check probes comprising nucleotides complementary to a nucleotide present in no degenerate base pairing set. These check probes establish that a failure of hybridization is indeed because of the presence at the relevant position(s) in the sequence of interest of the nucleotide not represented in any of the degenerately pairing nucleotide complementarity sets. An ultimate check probe, a null hybridizing sequence that is complementary at all probed for positions of a probed segment to the unrepresented complementarity of the overlapping degenerate complementarity sets comprises a nucleic acid sequence complementary to that segment and does not hybridize to any of the degenerately hybridizing probes. By having the nucleotide represented in none of the sets of nucleotides pairing to the null probe at all the tested positions in the segment, the presence of a nucleic acid sequence to which none of the primary, degenerately pairing, probes hybridizes is established. When only one of the tested or variable positions in a sequence segment is probed, the failure to hybridize of those probes having the multiply pairing nucleotides at one of the variable positions probed in the nucleic acid sequence segment indicates the presence, in the probed sequence position, of the nucleotide not present in the overlapping degenerately base pairing sets.

Any hybridization dependent attribute of a system may be determinately followed or studied by the method of the invention using a reduced number of hybridizing sequences or probes. The ability to streamline the process or experiment and derive the same quantum of information may be employed in both direct hybridization based sequencing and in sequencing by hybridizing tags that carry a label such as a label nucleotide sequence or a fluorescent or other spectroscopically or otherwise distinguishable moiety. Enzymatic amplifications requiring hybridized nucleic acid probes, including PCR primers and the like, may be studied. Methods of studying nucleic acid hybridization in living cells may also employ degenerate base pairing probes having incompletely overlapping complementarity sets.

Typically, for four possible nucleotides present in a sequence, use of doubly degenerate base pairing positions overlapping in one nucleotide in their base pairing sets, permits half the number of probes or hybridizing sequences, while the data may be analyzed to yield the same amount of information as if non-degenerately base pairing probes had been used. If six nucleotides are present in the nucleic acid sequence of interest, each label nucleotide sequence comprises, at the position corresponding to the variable position a nucleotide base pairing with four nucleotides, and five probe nucleotide or hybridizing sequences must be employed.

For example, the invention provides a method for determining a nucleotide at a position of interest in a nucleic acid sequence under conditions suitable for hybridization having a one base pair mismatch stringency, e.g., wherein a single base pair mismatch does not hybridize. The method comprises hybridizing to the target or analyte nucleic acid sequence a first probe comprising a nucleic acid sequence complementary, or complementary except at the probed position or position of interest, to the nucleic acid sequence. It is provided that the position of the first probe corresponding to the position of interest comprises a nucleotide base pairing with a first set of two nucleotides of four present in the nucleic acid sequence, and that a nucleotide present in the nucleic acid sequence is not represented in both the first set and the second set of two or more nucleotides. Under the conditions hybridization of the first probe (and the second probe) to the nucleic acid sequence occurs only if complementarity exists between the nucleotide at the position of interest and the nucleotide at the corresponding position of the first probe. Also employed for hybridizing to the nucleic acid sequence is a second probe comprising a nucleic acid sequence complementary or complementary except at the position of interest, to the nucleic acid sequence. It is provided that the position of the second probe corresponding to the position of interest comprises a nucleotide base pairing with a second set of two or more nucleotides present in the nucleic acid sequence. It is further provided that a nucleotide present in the nucleic acid sequence that is not represented in the second set of two or more nucleotides is not represented in the first set of two or more nucleotides. Also, the first set of two or more nucleotides present in the nucleic acid sequence includes one nucleotide that is a member of the second set of two or more nucleotides present in the nucleic acid sequence, the first set of two or more nucleotides and the second set of two or more nucleotides are not identical, and a nucleotide present in the nucleic acid sequence that is not represented in the first set of two or more nucleotides is not represented in the second base pairing set of two or more nucleotides.

For four nucleotides two probes per sequence position are required instead of four per sequence position using non-degenerately pairing probe positions, and cumulative information as to the identity of the nucleotide at the position of interest is obtained from the combined data from the first and second probes, both, neither or one or the other pairing with the probed position.

BRIEF DESCRIPTION OF THE DRAWINGS

FIG. 1 shows the degenerately pairing nucleotide dP.

DETAILED DESCRIPTION OF THE INVENTION

Figure 1A:
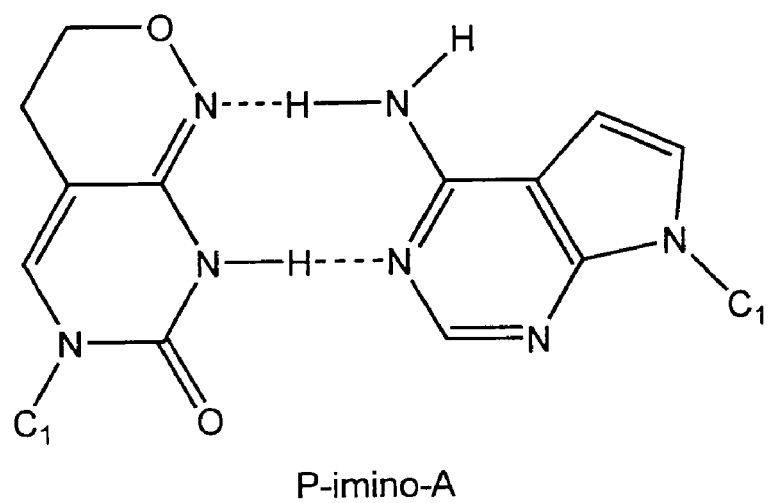
FIG. 1A shows the imino form of dP pairing with Adenine (A).

In describing and claiming the present invention, the following terminology will be used in accordance with the definitions set out below.

The term "adsorb" as used herein refers to the noncovalent retention of a molecule by a substrate surface. That is, adsorption occurs as a result of noncovalent interaction between a substrate surface and adsorbing moieties present on the molecule that is adsorbed. Adsorption may occur through hydrogen bonding, van der Waal's forces, polar attraction or electrostatic forces (i.e., through ionic bonding). Examples of adsorbing moieties include, but are not limited to, amine groups, carboxylic acid moieties, hydroxyl groups, nitroso groups, sulfones and the like. Often the substrate may be functionalized with adsorbent moieties to interact in a certain manner, as when the surface is functionalized with amino groups to render it positively charged in a pH neutral aqueous environment. Likewise, adsorbate moieties may be added in some cases to effect adsorption, as when a basic protein is fused with an acidic peptide sequence to render adsorbate moieties that can interact electrostatically with a positively charged adsorbent moiety.

The term "attached," as in, for example, a substrate surface having a moiety "attached" thereto, includes covalent binding, adsorption, and physical immobilization. The terms "binding" and "bound" are identical in meaning to the term "attached."

The term "array" used herein refers to a two-dimensional arrangement of features such as an arrangement of reservoirs (e.g., wells in a well plate) or an arrangement of different materials including ionic, metallic or covalent crystalline, including molecular crystalline, composite or ceramic, glassine, amorphous, fluidic or molecular materials on a substrate surface (as in an oligonucleotide or peptidic array). Different materials in the context of molecular materials includes chemical isomers, including constitutional, geometric and stereoisomers, and in the context of polymeric molecules constitutional isomers having different monomer sequences. Arrays are generally comprised of regular, ordered features, as in, for example, a rectilinear grid, parallel stripes, spirals, and the like, but non-ordered arrays may be advantageously used as well. An array is distinguished from the more general term pattern in that patterns do not necessarily contain regular and ordered features. The arrays or patterns formed using the devices and methods of the invention have no optical significance to the unaided human eye. For example, the invention does not involve ink printing on paper or other substrates in order to form letters, numbers, bar codes, figures, or other inscriptions that have optical significance to the unaided human eye. In addition, arrays and patterns formed by the deposition of ejected droplets on a surface as provided herein are preferably substantially invisible to the unaided human eye. Arrays typically but do not necessarily comprise at least about 4 to about 10,000,000 features, generally in the range of about 4 to about 1,000,000 features.

The terms "biomolecule" and "biological molecule" are used interchangeably herein to refer to any organic molecule, whether naturally occurring, recombinantly produced, or chemically synthesized in whole or in part, that is, was or can be a part of a living organism, or synthetic analogs of molecules occurring in living organisms including nucleic acid analogs having peptide backbones and purine and pyrimidine sequence, carbamate backbones having side chain sequence resembling peptide sequences, and analogs of biological molecules such as epinephrine, GABA, endorphins, interleukins and steroids. The term encompasses, for example, nucleotides, amino acids and monosaccharides, as well as oligomeric and polymeric species such as oligonucleotides and polynucleotides, peptidic molecules such as oligopeptides, polypeptides and proteins, saccharides such as disaccharides, oligosaccharides, polysaccharides, mucopolysaccharides or peptidoglycans (peptido-polysaccharides) and the like. The term also encompasses two different biomolecules linked together, for example a hybridization probe or adapter linked to the green fluorescent protein, or another luminescent molecule including a chemiluminescent molecule. The term also encompasses synthetic GABA analogs such as benzodiazepines, synthetic epinephrine analogs such as isoproterenol and albuterol, synthetic glucocorticoids such as prednisone and betamethasone, and synthetic combinations of naturally occurring biomolecules with synthetic biomolecules, such as theophylline covalently linked to betamethasone.

The term "biomaterial" refers to any material that is biocompatible, i.e., compatible with a biological system comprised of biological molecules as defined above.

The terms "library" and "combinatorial library" are used interchangeably herein to mean a plurality of chemical or biological moieties. Such moieties my be present in separate containers, including an array of well plate wells, or present on the surface of a substrate such as attached to discrete beads which may be arrayed, or wherein each moiety is present attached or not attached arrayed on a substrate surface with or without physical or spatial barriers separating one discrete region having an individual moiety from another so long as each moiety is different from each other moiety. The moieties may be, e.g., peptidic molecules and/or oligonucleotides.

The term "moiety" refers to any particular composition of matter, e.g., a molecular fragment, an intact molecule (including a monomeric molecule, an oligomeric molecule, and a polymer), or a mixture of materials (for example, an alloy or a laminate).

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Suitable analogs will be known to those skilled in the art and are described in the pertinent texts and literature. Common analogs include, but are not limited to, 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-oxoguanine (8-oxo-G), 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl) uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, 6-(beta-d-ribofuranosyl)-3,4-dihydro-8H-pyrimido[4,5-c]-[1,2]oxazin-7-one (P), queosine, inosine, 1-methylinosine, hypoxanthine, xanthine, 2-aminopurine, 6-hydroxyaminopurine, 6-thiopurine and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "oligonucleotide" shall be generic to polydeoxynucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones (for example PNAs), providing that the polymers contain nucleobases in a configuration that allows for base pairing and base stacking, such as is found in DNA and RNA. Thus, these terms include known types of oligonucleotide modifications, for example, substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the term "polynucleotide" and "oligonucleotide," and these terms will be used interchangeably, but do not not include monomers, thus a minimum length of two nucleotides is contemplated by these terms. These terms refer only to the primary structure of the molecule. As used herein the symbols for nucleotides and polynucleotides are according to the IUPAC-IUB Commission of Biochemical Nomenclature recommendations (*Biochemistry* 9:4022, 1970).

The term "substrate" as used herein refers to any material having a surface onto which one or more fluids may be deposited. The substrate may be constructed in any of a number of forms such as wafers, slides, well plates, membranes, for example. In addition, the substrate may be porous or nonporous as may be required for any particular fluid deposition. Suitable substrate materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose and spun synthetic polymers such as spun polyethylene), metallic compounds (particularly microporous aluminum), or the like. While the foregoing support materials are representative of conventionally used substrates, it is to be understood that the substrate may in fact comprise any biological, nonbiological, organic and/or inorganic material, and may be in any of a variety of physical forms, e.g., particles, strands, precipitates, gels, sheets, tubing, spheres, containers, capillaries, pads, slices, films, plates, slides, and the like, and may further have any desired shape, such as a disc, square, sphere, circle, etc. The substrate surface may or may not be flat, e.g., the surface may contain raised or depressed regions. A substrate may additionally contain or be derivatized to contain reactive functionality that covalently links a compound to the surface thereof. These are widely known and include, for example, silicon dioxide supports containing reactive Si—OH groups, polyacrylamide supports, polystyrene supports, polyethyleneglycol supports, and the like.

The term "surface modification" as used herein refers to the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

The phrase "base pairing" as used in this application is intended to encompass all manner of specific pairings between the bases that make up nucleic acid sequences. Specifically contemplated are the most typically observed Watson-Crick base pairings between antiparallel sequences in which the pairing scheme is {[A::T or U], [G::C]} with the former pairing being stabilized by two hydrogen bond interactions and the latter being stabilized by three H bonds. Also encompassed are Hoogstein, triplex and wobble base pairing interactions, and the like. The base pairing may be between two free nucleotides or nucleosides, or a free nucleotide or nucleoside and a position of a nucleic acid sequence, or between nucleic acid sequences at individual corresponding positions of a nucleic acid hybridized structure.

The adjectival term "hybridized" refers to two or more sequentially adjacent base pairings. The term "hybridization" refers to the process by which sequences become hybridized. The verb to hybridize and gerund form hybridizing refer to experimental or attempted hybridization by contacting nucleic acid sequences under conditions suitable for hybridization.

The term "complementarity" or "complementary" as used in this application denotes the capacity for cumulative base pairing between nucleic acid sequences at individual corresponding positions, as in a nucleic acid hybridized structure. "Complete" or "perfect" complementarity describes a stabilizing base pairing interaction at each sequence position to corresponding sequence position in a nucleotide sequence. "Partial" complementarity describes nucleic acid sequences that do not base pair at each position. A single mismatch partial complementarity refers to sequences that base pair at every position but one.

The phrase "complementarity set" or "base pairing set" as used in this application refers to the set of nucleotides that base pair to an analyte, probed or target nucleic acid sequence at a variable or probed position or position of interest. The complementary sequence therefore may comprise at the position corresponding to the position of interest or variable position of the analyte sequence any of the members of the complementary set. The complementarity or base pairing set includes nucleotides that are complementary in the context of single stranded sequence hybridization and/or incoming nucleotide base pairing for nucleic acid polymerase synthesis from a template. The phrase complementarity set used in reference to a sequence of two or more nucleotides refers to the set of all the sequences that are complementary, capable of hybridizing, to that sequence.

The phrase "overlapping complementarity sets" refers to complementarity sets that have one or more nucleotides in common, or one or more sequences in common. Unique complementarity sets will not completely overlap, with such sets related as set/subset or partial overlap relationship. Examples of overlapping complementarity sets having partial overlap are the complementarity sets of the degenerately pairing nucleotide analogs dPTP (complementarity set: {A, G}) and 8-oxo-dGTP (complementarity set: {A, C}). Thus the complementarity sets of P and 8-oxo-G are unique and of the partial overlap type, having a common base A an excluded base T. Each set has a non-common or unique base, for P, G and for 8-oxo-G, C are the respective unique bases in the partially overlapping complementarity sets.

The phrase "hybridizing conditions" or "conditions suitable for hybridization" or like phrases used herein contemplates those conditions necessary for hybridization, e.g. those conditions appropriate to permit hybridization of nucleic acids taught by the invention. The specific chemical and physical conditions appropriate, suitable or effective for hybridization as practiced in the invention are known or ascertainable by those of skill in the art of nucleic acid detection and assay. Conditions suitable for hybridization include a range of conditions adequate for forming any hybridized nucleic acid species required for hybridization by the methods of the invention, and include a range of hybridization conditions having various stringencies. Thus the range of hybridization conditions includes conditions effecting high, medium and low stringency nucleic acid hybridization including a stringency sufficient to preclude formation of significant amounts of double stranded complementary structures in a given length of sequence for one, internal or external mismatch. Less stringent hybridization conditions are capable of discerning only a greater sequence mismatch using hybridization.

The term "hybridization probe" as used herein refers to a nucleic acid sequence that by itself or as a member of a set of nucleic acid sequences or probes for a specific nucleic acid sequence, effects the hybridization of a specific target sequence. The hybridization probes of the invention comprise a nucleic acid sequence segment having sequence complementary to the analyte sequence of interest. Such probes may comprise nucleic acid sequence for potential hybridization with analyte only, or may additionally comprise a discrete tagging or labeling moiety, such as a chemiluminescent moiety or a discrete nucleic acid sequence that is not a putative anti-target or anti-analyte sequence, but functions solely to indicate the presence of the probe. Such hybridization probes include sequences that form hybrids for enzymatic amplification such as primers for polymerase chain reaction amplification and sequences forming double stranded complex replication templates for enzymes such as the RNA replicases. In addition to hybridizing probes for an amplification process, probes for simple hybridization and detection, both tagged or labeled with a discrete moiety and not labeled with any discrete label moiety are contemplated. Nucleic acid sequences comprising probes not having a discrete labeling moiety may be intrinsically labeled for detection of the hybridization, as by incorporation of $^{32}P$ into the nucleic acid phosphodiester backbone or the like. Hybridization probes may comprise a sequence complementary to the sequence to be detected and detectable signal or marker indicating the presence of the complementary sequence, for example a separate moiety such as a chemiluminescent marker, or $^{32}P$ incorporated into the phosphodiester backbone of the nucleic acid sequence or both.

The phrase "analyte sequence" or "probed sequence" or "target sequence" refers to a nucleic acid sequence that is to be detected.

Hybridization based procedures are important in amplification and detection of nucleic acid sequences generally, and in amplification and/or detection for sequencing. The amplification of nucleic acids typically employs hybridizing probes such as the primers used in polymerase chain reaction (PCR) (see generally U.S. Pat. Nos. 4,683,195 and 4,683,202 to Mullis et al.) and the hybridizing probes that are used to achieve amplification of such probes when they form a complex template substrate for an RNA replicase enzyme (see generally U.S. Pat. No. 4,786,600 to Kramer; U.S. Pat. Nos. 5,407,798 to Martinelli et al. and 6,090,589 to Dimond et al.). The methods that employ RNA replicases obtain amplification by the amplification of an amplification probe sequence rather than by direct amplification of a segment or segments of target nucleic acid analyte. Methods based upon PCR specifically amplify a target sequence that requires a specific hybridized primer. Consequently, the RNA replicase amplification probe or probes employed must be carefully designed to both form the correct complex template required by the replicase enzyme, and to effect amplification of the correct probe. Analogously PCR probes must also be carefully designed to effectuate the amplification of the probed for sequence.

The use of hybridization for sequencing involves either direct use of hybridization data, wherein the sequence of an unknown or analyte sequence is obtained by hybridization to known nucleic acid sequences with overlapping sequence under conditions that permit no mismatches in base pairing (U.S. Pat. Nos. 5,492,806, 5,525,464 and 5,695,940 to Drmanac et al.).

Sequencing by hybridization (SBH) of a target nucleic acid may be described as a two step process: (i) disassembling the target nucleic acid into all its constituent oligonucleotides of length N(N-mers); and (ii) the deduction of the sequence by assembly of N-mers detected by hybridization in a sequential N-mer arrangement indicated by sequence overlap into an extended sequence. In classical SBH of this type, hybridization of all possible N-mer oligonucleotide hybridization probes to the target nucleic acid determines the N-mer oligonucleotide subset contained in the primary sequence of the target nucleic acid and is the first step in the process. The methods and partially overlapping degenerate base pairing positions of the nucleic acid sequences of the invention permit, for nucleic acids having four possible nucleotides, permit employment of half the number of probes as the number of N-mers.

For example, for 8-mers, $4^8$ possible sequences exist but the invention permits using only $2*4^7$ sequences for obtaining the sequence. For a single variable position per hybridization probe, $4^7$ possible sequences exist not including the variable position, and the variable position has two possible partially overlapping degenerate base pairing or complementary sets, thus permitting $2*4^7$ possible probes. If two variable positions are employed $4^6$ possible sequences exist for positions that are not variable, and each variable position has two possible partially overlapping degenerate base pairing or complementary sets, thus permitting $2*2*4^6$ ($4^7$) possible probes. However, use of two variable positions complicates both data acquisition and analysis, as base pairing or the lack thereof must be independently detected and analyzed; for example in addition to high stringency hybridization where a single mismatch precludes hybridization experiments permitting single mismatch hybridization but prohibiting double mismatch hybridization must be employed with the additional capacity to determine at which variable position the single mismatch occurs would be required for data acquisition and the data analysis would be twice as computationally complex. This could, for example, be obtained by employing a probe having a terminal and internal variable position in conjunction with calorimetric methods, such as differential scanning calorimetry (DSC).

The preceding SBH methods may be practiced by employing an array of hybridization probes attached to a substrate surface, or an array of separate beads. Or, the beads or free (unattached) hybridization probes may be present in a plurality of different assay containers either arrayed in well plate wells, or the containers may be discrete. Integrated infrared video imaging with integration for discrete array sites may conveniently be employed to detect hybridization and to differentiate different stabilization energies for example in two variable position hybridization probes.

A nucleic acid fragment can be deconstructed into all constituent oligonucleotides. Positively hybridizing N-mer oligonucleotide probes are sequentially ordered and the sequence of the analyte DNA is determined using (N–1)mer overlapping frames between the oligonucleotide probes.

The sequence is deduced by reassembly of the sequence of known (N–1)-mer overlapping oligonucleotides that hybridize to the target nucleic acid to generate the sequence of the target nucleic acid, which cannot be accomplished in some cases because some information is lost if the target nucleic acid is not in fragments of appropriate length in relation to the size of the oligonucleotides that are used for the hybridization probes. The quantity of information lost is proportional to the length of a target being sequenced. However, if sufficiently short targets are employed, their sequence can be unambiguously determined. The deductive construction of the sequence is interrupted in analyte sequence regions where a given overlapping (N–1)-mer is duplicated to appear at least three times in succession, e.g. repeated two or more times, causing the deduced sequence to skip the second and subsequent repetitions in sequence. At such points either of two different N-mers, differing in the last nucleotide are deduced for extending the sequence construction. Such branching points of sequence deduction limit unambiguous assembly of a sequence.

The probabilistic distribution frequency of such duplicated sequences that interfere with sequence deduction for a certain length of DNA can be calculated. As sequence motifs and patterns are not completely random in their distribution among species and between types of sequence, it will be readily appreciated that often the best approach for calculating this probabilistic distribution frequency will be a species-specific genomic heuristic bioinformatics approach. The derivation of a probabilistic distribution frequency function requires a parameter pertaining to sequence organization termed in the art the sequence subfragment (SF).

As defined in the art, a sequence subfragment exists if any part of the sequence of a target nucleic acid starts and ends with an (N–1)-mer that is repeated two or more times within the target or analyte sequence. Thus, subfragments are sequences generated between two points of branching in the process of assembly of the sequences in the method of the invention. As defined to include the short double or greater repeat, the sum of lengths of all subfragments is longer than the actual target nucleic acid because of overlapping short ends. Generally, subfragments cannot be assembled in a linear order without additional information since they can possibly have the same repeated (N–1)-mers at their ends and starts. Different numbers of subfragments are obtained for each nucleic acid target depending on the number of doubly repeated (N–1)-mers. Their number depends on the value of N–1, the length of the target and the type and species of derivation of the nucleic acid sequence. Sequence "type" is intended to denote intron, exon and regulatory sequence of genomic nucleic acid, and distinctions between conventional genomic and mRNA transcript sequence, and viral genomic transcript and reverse transcriptase transcript.

Thus for the analyte sequence (the ribonucleotide U and the deoxyribonucleotide T are used interchangeably for base pairing purposes) 5'-ATAAAGCTGCTTC (SEQ ID. NO. 1) (having no subfragments) will hybridize only to beads or array sites having the 5-mers 5'-ATAAA, 5'-TAAAG, 5'-AAAGC, 5'-AAGCT, 5'-AGCTG, 5'-GCTGC, 5'-CTGCT, 5'-TGCTT, and 5'-GCTTC under stringency conditions permitting no mismatch among the five nucleotides available for base pairing. There are $4^5$ or 1024 possible 5-mers that can be arrayed on a substrate or present attached to individual beads, but even those similar to the nine perfectly matching 5mers listed above will have sufficiently different energies of hybridization that under stringent conditions analysis of the hybridization data directly will permit sequencing the analyte nucleic acid sequence. Much longer unknown sequences can be readily sequenced segment by segment in this manner, with appropriate consideration of the subfragment problem. In some cases the subfragment ordering may require application of another sequencing method, such as the ligation signature hybridization method (below) and traditional gel electrophoresis methods (Maxam and Gilbert (1977) supra; Sanger, et al. (1977) supra).

Another sequencing method that relies upon hybridization employs a label or tag that identifies the specific hybridizing sequence. For example a different fluorescent marker can be linked to each possible sequence of three nucleotides ($4^3$ or 64 in all), and a sequence may be obtained by successive hybridization and digestion of three nucleotides at a time. The sequence may also be obtained by labels comprising a nucleotide sequence, for example the start codon AUG may be labeled by the sequence 5'-AAAAAAAAAC-CCCCTTTTCTTTT (SEQ ID NO: 2), which will form a hairpin loop self complementary structure that can be differentiated from like labeling structures, such as 5'-AAAAAAAAACCCCCTTTTTTTTT) (SEQ ID NO: 3) and 5'-AAAAGAAAACCCCCTTTTCTTTT (SEQ ID NO: 4), by the temperature that causes a loss of such secondary structure.

"Wobble" is a phenomenon of degenerate base pairing in codon anticodon recognition (Stryer *Biochemistry*, $4^{th}$ Ed. (1999), W. H. Freeman & Co., New York). The existence of 64 codons for 20 amino acids requires that codon degeneracy exist, that is that several codons code each of the amino acids. Without degeneracy in base pairing termed "wobble" up to four tRNA adapters would be required for each of the twenty amino acids in translation into peptide sequence, requiring more amino acid and tRNA specific linking enzymes, and increasing the potential for both stochastic and genetically induced or predisposed errors in translation. Thus the degeneracy of base pairing or wobble of the tRNA interaction with the codon sequences of the mRNA transcript permits more efficient translation in the context of the degeneracy of the correspondence of codons to amino acids, by compensating for the degeneracy of the code via the degeneracy of code recognition in a determinate manner. That is, the identity of the amino acid that is coded by the degenerate or multiple set of codons is known or determinate, and the degeneracy of the codon correspondence is compensated exactly by the wobble interaction at the third position of the codon in such a manner as to always render the correct amino acid at the position in the amino acid sequence corresponding to a specific codon of interest.

Figure 1B:
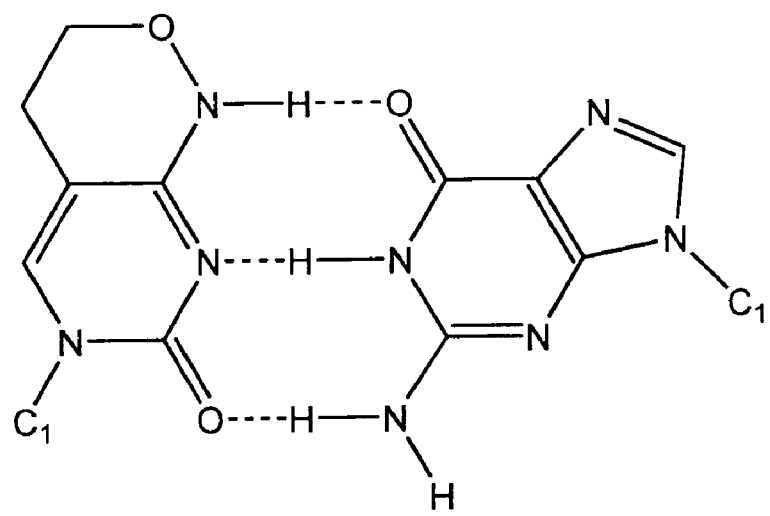
FIG. 1B shows the amino form of dP pairing with Guanine (G).

Degenerate base pairing has been used to render non-determinate or "undeterminate" results. For example the nucleic acid analog, dPTP, (Amersham, Cambridge UK) can behave as either dT or dC, depending upon the tautomeric form that participates in the base pairing interaction (FIG. 1). Thus dP in a position in a nucleic acid sequence pairs with both A (as dT) and G (as dC) approximately equally, indicative of equivalent binding energies. Thus dP may be incorporated in a nucleic acid sequence for either T or C equally in a proportion relative to the concentration of T or C in the polymerization mixture. When replicated a position incorporating dP is polymerized as the complementary sequence to the template having dP incorporated at the position of interest, causing either dT or dC to be incorporated at that position because of the relatively small difference in free energies between the two tautomers (a property which facilitates but is not absolutely required for the equivalence in base pairing energies noted above). As the imino form of dP resembles dT and thus pairs with dA (FIG. 1A) and as the amino form of dP emulates dC to pair with dG (FIG. 1B). Actually the imino tautomer base pairs with A with two H bonds, while the amino form base pairing with G with three H bonds, analogous to the Watson-Crick base pairings between the four nucleotides that normally appear in DNA and form the genetic code, A, T, G and C. This difference in base pairing energies makes GC rich sequence have a lower transition or "melting" temperature ($T_m$) of double stranded hybridized to single stranded. The difference in energies between dP::C and dP::T interactions is actually less than the 1 Kcal/mole contribution of the single H bond difference between A::T and G::C, as tautomeric intercoversion into a mismatch can occur in the dP interactions and exists over a statistically small proportion of time for both interactions. The difference in H bonding energies from one base pair and consequent difference in $T_m$ can be rendered insignificant by probe design strategies such as lengthening the probe. Alternatively the use of agents such as tetramethylammonium chloride abolish the energetic and $T_m$ difference from the G::C versus A::T interaction difference.

A may be randomly transmuted to G, and G may be stochastically transformed to A by use of dP in the replication mixture, because dATP and dGTP are necessarily present in the reaction mixture, and the replicated complementary sequence position base pairs approximately equally with these dNTPs as incoming nucleotides in polymerization. If dC and dT are present in the polymerization mixture, then because the sequence having random substitution of A for G and G for A, forms a template for further polymerization in which the complementary substitution of T for C occurs (and C for T). Thus, dPTP is used as a nucleotide substrate of the polymerase in conjunction with PCR to randomly or stochastically interchange A and G and consequently complementary interchange T and C. This is therefore a PCR mediated random mutagenesis, interconverting A and G and C and T.

Figure 2:
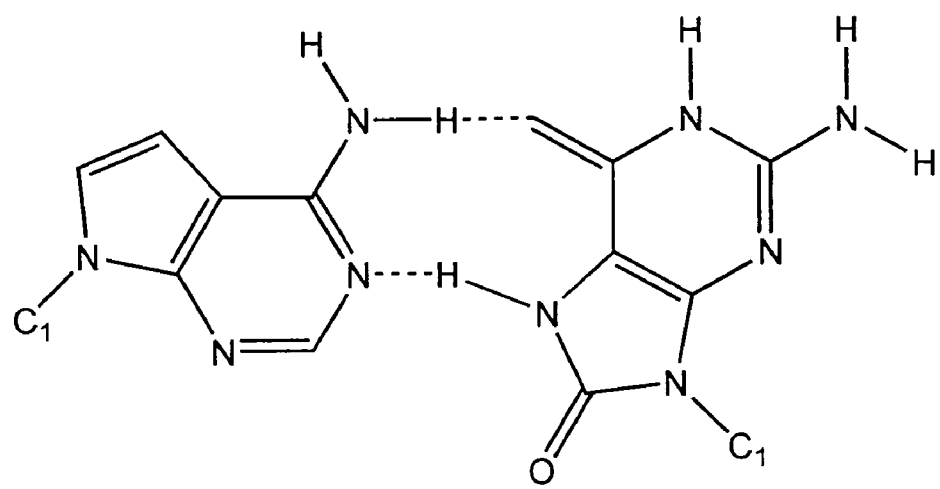
FIG. 2 shows the degenerately pairing nucleotide 8-oxo-G pairing to A in a base pairing interaction resembling a wobble base pair.
Figure 3:
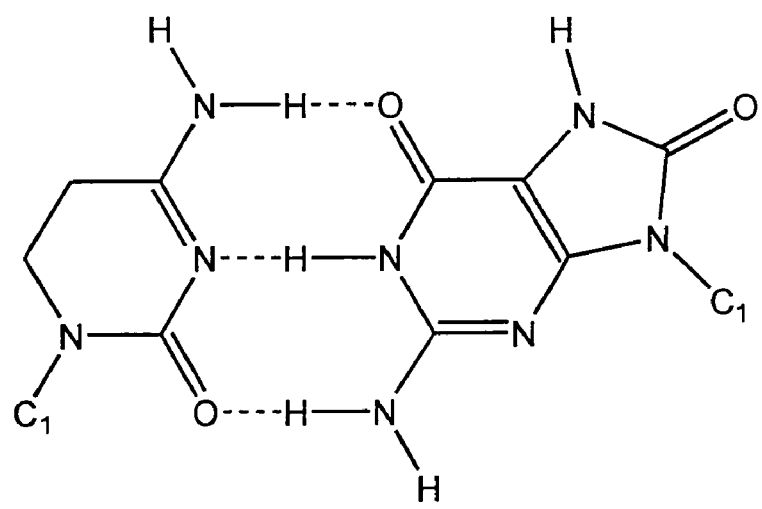
FIG. 3 shows the degenerately pairing nucleotide 8-oxo-G pairing to C in conventional Watson-Crick base pairing interaction substantially the same as a G::C base pairing interaction.

The nucleic acid analog 8-oxo-dGTP (Amersham, Cambridge UK) is formed spontaneously by oxidation of dGTP in the context of normal cellular metabolic activity. 8-oxo-dGTP has one form which can behave as either dG to pair with C (FIG. 2) in a standard base pairing steric arrangement or as dT to pair with A (FIG. 3) in a sterically atypical base pairing arrangement resembling a wobble base pairing arrangement. Thus 8-oxo-dG at a position in a nucleic acid sequence pairs with both C (as dG) and A (as dT) in close amounts indicative of moderately different binding energies. Thus 8-oxo-dG may be incorporated in a nucleic acid sequence for either G or T almost equally in a proportion relative to the total number of G or T in the polymerization mixture. When replicated a position incorporating 8-oxo-dG is polymerized as the complementary sequence to the template having 8-oxo-dG incorporated at the position of interest as a G, therefore causing only dC to be incorporated at that incoming nucleotide position because of the difference in free energies between the two base pairing interactions, e.g. 8-oxo-dG::C versus 8-oxo-dG::A. FIG. 2 shows that 8-oxo-dG::C has three H bonding interactions compared to two for 8-oxo-dG::A (FIG. 3), which is not a standard Watson-Crick base pairing interaction. Because in a polymerase reaction mixture containing all the nucleotides plus 8-oxo-dG, a proportion of sequence positions having a T (pairing A) are substituted with 8-oxo-dG, which then pairs with C, the purine A is effectively converted to the pyrimidine C, and T is converted to G. Such random or stochastic transmutation is from purine to pyrimidine and visa versa, a transmutation termed transversion. Note that dGTP could be absent from the polymerase mixture and wholly replaced by 8-oxo-dG, but this will not typically be the case. Because dTTP and 8-oxo-dGTP are necessarily present in the reaction mixture, the replacement of T with 8-oxo-dG will be proportionate to the relative amounts, and therefore concentrations of the two dNTPs. For replication, the presence of the 8-oxo-dG causes the incoming nucleotide for the complementary nascent strand synthesized from the 8-oxo-dG containing template to be dC exclusively, and the dC then causes a dG to be inserted for subsequent polymerization using the new strand as a template. Thus the 8-oxo-dG in a sequence behaves as a G for the purpose of synthesis from a template containing the 8-oxo-dG. If all four standard dNTPs (A,T,C,G) are present in the polymerization mixture along with 8-oxo-dG, then the sequence having random substitution of 8-oxo-dG for T forms a template for further polymerization in which the complementary substitution of A for C occurs along with the complementary substitution of T for G. Such mutations from purine to pyrimidine and visa versa are known as transversion mutations. Thus although mechanistically somewhat different than the random mutagenesis effected via dPTP, while still depending upon degenerate base pairing, 8-oxo-dG is used as a nucleotide substrate of the polymerase in conjunction with PCR to randomly or stochastically interchange T and G and consequently complementary interchange A and C. This is therefore a PCR mediated random transversion mutagenesis, converting T to G and A to C, but not the converse (e.g., neither G to T nor C to A).

Although an incoming nucleotide added opposite an 8-oxo-dG is normally a C, evidencing a more energetically stabilized base pairing for 8-oxo-dG::C than 8-oxo-dG::A, the 8-oxo-dG still has degenerate base pairing properties that cause it to pair with A at a position in the template to cause incorporation of 8-oxo-dG for T, and these same base pairing properties permit hybridization between a sequence containing the 8-oxo-dG at a position in the sequence and an A in the corresponding position. Although the base degenerate base pairing properties of the deoxyribonucleoside triphosphate analogs 8-oxo-dG and dPTP are employed in an indeterminate or non-determinate manner to induce the random mutagenesis described above, nucleotides comprising nucleosides having degenerate complementarity sets that partially overlap as do the base pairing complementarity sets of 8-oxo-dG (base pairing complementarity set={C, A}) and dPTP (base pairing complementarity set={G, A}), which overlap in the common A and both exclude the nucleotide T, can be used in a determinate manner.

Likewise, a specific sequence position of two probes, each having partially overlapping base pairing sets of two possible nucleotides at that sequence position, such as two probes for hybridization having a sequence 5'-AT($X_i$)GG linked to a chemiluminescent (ChL) or other tag, 5'-AT(dP)GG-CL, and 5'-AT(dP)GG-CL$_2$, where ChL$_1$ and ChL$_2$ are chemiluminescent at different frequencies, and $X_1$ comprises T or C in equal proportions, and $X_2$ comprises G or T in equal proportions making the third ($X_1$) position of 5'-AT($X_1$)GG-ChL$_1$ pair degenerately to the set of nucleotides G and A (base pairing complementarity set={G, A}), and the third ($X_2$) position of 5'-AT($X_2$)GG-ChL$_2$ pair degenerately to the set of nucleotides C and A (base pairing complementarity set={C, A}). Thus 5'-AT($X_2$)GG-ChL$_2$ is the effective equivalent to the degenerately pairing hybridization probe 5'-AT(dP)GG-ChL$_2$, which utilizes, instead of equal proportions at the third position of C and T, the deoxynucleoside analog dP which base pairs, for the purpose of hybridization, almost equally with G and A. Analogously 5'-AT($X_1$)GG-ChL$_1$ is the equivalent to 5'-AT(8-oxo-dG)GG-ChL$_1$, with the degenerately pairing analog 8-oxo-dG, which pairs, for the purposes of hybridization, nearly equally with A and C, at the third position instead of equal proportions of T and G. Both sets of hybridization probes {5'-AT(dP)GG-ChL$_2$, 5'-AT(8-oxo-dG)GG-ChL$_1$} and {5'-AT($X_2$)GG-ChL$_2$, 5'-AT($X_1$) GG-ChL$_1$} as well as sets in which a degenerately base pairing nucleoside analog is employed for one of the probes, while equal proportions of nucleosides having the desired base pairing properties may be employed, as long as the base pairing sets overlap in the manner described, e.g. for two doubly degenerate base pairing sets, overlap of one of the nucleotides. Two unique doubly degenerate base pairing sets, e.g. each base pairing complementary set containing two nucleosides that are about equally paired for hybridization purposes, are required for normal nucleic acid sequences having four possible nucleotides (the ribonucleoside Uracil (U) being equivalent for these purposes to T).

If the sequence to be analyzed contains or may contain additional nucleotides, more sets having overlap are required for determinate use of the degenerate base pairing. For example, if six nucleotides could be in the sequence, five quadruply degenerate pairing probes could be employed. Each of these five probes must have at the position of interest or probed position a unique base pairing set containing one of the six possible nucleotides, so that all the sets contain the specific nucleotide, and one of the six possible nucleotides must be absent from all the base pairing sets. Further, each unique base pairing set, in addition to overlapping with the remaining four base pairing sets in the nucleotide common to all five sets, for example, also overlaps in two other of the possible nucleotides with any other probe. This additional overlap of two nucleotides cannot be the same for all pairs of quadruply degenerate probes if all the base pairing sets are unique. In this manner all five quadruply degenerate pairing probes would hybridize to the specific sequence in which the common base of the base pairing set is present at the position of interest, and none of the probes would, under appropriately stringent hybridization conditions, hybridize to the sequence in which the base absent from all five quadruply degenerate base pairing sets is present at the position of interest. When the other four nucleotides are present at the position of interest, the system is constructed such that four of the five specific probes will hybridize to the analyte sequence.

The situation is much simpler for the typical case of four possible nucleotides in a hybridizing sequence, where two probes having unique doubly degenerate partially overlapping base pairing sets at one position may be employed in a determinate fashion. For example probe sets such as {5'-AT(dP)GG-ChL$_2$, 5'-AT(8-oxo-dG)GG-ChL$_1$}, {5'-AT($X_2$)GG-ChL$_2$, 5'-AT($X_1$)GG-ChL$_1$}, {5'-AT($X_2$)GG-ChL$_2$, 5'-AT(8-oxo-dG)GG-ChL$_1$} and {5'-AT(dP)GG-ChL$_2$, 5'-AT($X_1$) GG-ChL$_1$} could be used to probe for the antiparallel sequence 5'-CCζAT where ζ is an unknown or variable base at the sequence position of interest or variable position. If 4 is T, none of the probes will hybridize to the analyte sequence, while both probes will hybridize to the analyte if ζ is A. If the identity of ζ is G only one of the probes will hybridize (either 5'-AT(dP)GG-ChL$_2$ or 5'-AT($X_2$)GG-ChL$_2$ depending upon which is employed), and if ζ is C only the other (only one) of the two probes will hybridize (either 5'-AT(8-oxo-dG)GG-ChL$_1$ or 5'-AT($X_1$)GG-ChL$_1$ again depending upon which is employed). This permits use of two probes instead of four if non-degenerate probes were employed with full knowledge of the identity of 4 and therefore a determinate use of the degenerate probes.

The preceding has been described in the context of tagged or labeled hybridization probes which may be employed for sequencing using tagged probes. First that the label or tag need not be chemiluminescent should be noted. For example a fluorescent or otherwise spectroscopically detectible tagging moiety may be employed. Alternatively the sequence that is expected to hybridize may be tagged or labeled with a nucleic acid sequence that does not hybridize by virtue of its properties, for example the tendency to form hairpin loops or some other non-hybridizing structure or a sequence that is known not to be complementary to any sequence in the analyte, such as polyA or polyT for genomic analyte (where mRNA tails are not present). Further, two "colors" or spectroscopically detectible frequencies of chemiluminescense are also described above, and facilitate a two color assay akin to two color hybridization as described in U.S. Pat. No. 5,800, 992 to Fodor et al. Although employing two colors facilitates probing simultaneously with the two probes by permitting simultaneous visualization of the two probes rather than multiple detection steps, to detect analyte sequences hybridizing to one ($1^{st}$ frequency) the second ($2^{nd}$ frequency) or both (composite of the two frequencies) probes, this is not requisite for practicing the invention. The two probes may be employed sequentially with a conventional tagging or labeling moiety that is the same for both probes. Additionally the probes need not be tagged or labeled by a discrete labeling moiety as is the case when methods for sequencing by hybridization that do not employ discrete tags or labels are employed (U.S. Pat. No. 5,525,464 to Drmanac et al.), and hybridization may be detected by detecting $^{32}$P autoradiographically. Alternatively hybridization can be detected without any label, whether a separate moiety or part of the nucleic acid, even the incorporation of $^{32}$P into probe or analyte, by thermal detection, as when an oligonucleotide array of probes is hybridized to analyte while recorded by an infrared video camera, and the integrated signal from each array site indicates the extent of hybridization of analyte thereto. Additionally detection of multiple analyte segments that, for example, comprise a hybridizing subset of analyte subsequences that are simultaneously exposed to a probe array, may be accomplished by detecting all hybridizing array positions without an explicit label moiety as described above.

Instead of probes at specific array positions, discrete beads may be employed, each bead linked to a specific probe or analyte nucleic acid sequence with the detection of which probes hybridize obtained with or without use of a discrete label moiety. Or, either the array or bead method may be employed with the array sites or beads attached to analyte sequence segments obtained by manipulations including, for example, PCR amplification. The probes are then hybridized to the array sites or specific beads and may be detected with or without the use of a discrete label or tag moiety as described above.

One such sequencing method is described by Brenner et al. (2000) *Nat. Biotechnol.* 18(6):630-34. The method involves parallel sequencing of cDNA templates "cloned" onto microbeads for a gene expression analysis. Other DNA sequences, including genomic DNA and reverse transcriptase polymerized RNA sequences may be analogously sequenced in such a parallel manner. The cDNA templates, each comprising a different analyte sequence are combinatorially conjugated to a set of oligonucleotide attachment tags where the number of oligonucleotide tags is at least about a hundred times the number of cDNA templates. Brenner et al. (2000), supra, implemented such in vitro cloning on microbeads for 3–4× $10^4$ different cDNA templates by combinatorially inserting the templates into a set of cloning vectors comprising 1.67× $10^7$ different 32-mer oligonucleotide tags to form 5–7×$10^{11}$ conjugates. A sample of the conjugates is taken corresponding to 1% of the total number of represented tags, about 1.67×$10^5$ of the 1.67×$10^7$ total tags employed. This sample size ensures that substantially every cDNA template represented in the sample is conjugated to a unique tag and that at least one of each of the 3–4×$10^4$ cDNA templates in the sample is represented in the sample with greater than 99% probability. This representative sample is then amplified by PCR. The tags in the PCR amplified sample are then rendered single stranded and this mixture is then contacted with a plurality of microbeads, each microbead having attached thereto an anti-tag sequence complementary to a specific tag sequence in a number of anti-tag copies attached to each bead of about $10^4$ to $10^5$ copies per bead. The plurality of microbeads comprises a set such that each anti-tag sequence is represented in the bead population, e.g. there are 1.67×$10^7$ different anti-tag sequence linked beads. Because the PCR amplified sample contains only 1% of the total number of tag sequences, only 1% of the bead population are "loaded" with tag conjugated cDNA template. Such loaded beads (the 1%) are separated or "concentrated" into a library of loaded microbeads by use of a fluorescense activated cell sorter (FACS). Each microbead of the library thus has $10^4$-$10^5$ identical copies of one cDNA template conjugated to the specific tag, hybridizing to the anti-tag sequences of the bead, attached to it.

Brenner et al. thus illustrate one method of attaching multiple identical copies of nucleic acid sequence to individual beads and will be readily apprehended as being readily adapted to attaching the nucleic acid sequences in multiple copies to discrete array sites. Further, other methods such as spotting or photolithographic methods, or simply the reaction of separate beads in separate wells to attach multiple copies of nucleic acid sequence may be appropriately applied to link or attach multiple analyte nucleic acid sequences to discrete array regions or sites, or to beads.

The cDNA templates as attached to beads in a copy number of $10^4$-$10^5$ identical sequence polymers per bead, the loaded bead library, which may be spatially arrayed as a spatial array of beads is at minimum a virtual array that permits parallel sequencing, which because of the number of beads sequenced simultaneously has been termed by the authors (Brenner et al. (2000), supra) Massively Parallel Signature Sequencing (MPSS). The specific method illustrated employs adaptors comprising nucleic acid sequences having four base overhangs linked via a common 14 nucleotide long linking nucleic acid sequence to a decoder binding site sequence of 10 nucleotides, and a common strand comprising a 14 nucleotide sequence complementary, and hybridized, to the common linker sequence. Thus each adapter comprises, reading 5' to 3' on the 28 nucleotide long strand that is unique for each adaptor, a single stranded four nucleotide linker sequence linked to a 14 nucleotide double stranded sequence, followed by a 10 nucleotide sequence which tags or labels the specific overhang sequence that hybridizes to the analyte sequence. The overhang sequences base pair with the analyte cDNA template sequences, and the decoder binding sites signify or uniquely label or encode the specific overhang sequence for detection. A signature is then obtained by detecting and monitoring the series of adapter ligations (by hybridization) resulting from a cycle of adapter ligation and detection followed by type IIs restriction endonuclease digestion. As illustrated by Brenner et al. (2000), supra, the MPSS method monitors a series of adapter ligations (overhang sequence hybridization) on the surface of a microbead in a fixed position of a flow cell.

The illustrated MPSS method exploits a property of type IIs restriction endonucleases, namely that the cleavage site is separated from the recognition site by a characteristic number of nucleotides. Thus the adapters may be constructed so that the type IIs recognition site is positioned in the adapter so cleavage of the ligated analyte-adapter will occur in the cDNA template analyte sequence to expose additional bases for hybridization with the adapter overhang sequence in the subsequent ligation. Thus each cycle of the MPSS method requires hybridization of an incoming adapter after IIs endonuclease digestion of an outgoing adapter. After ligation, the incoming adapter is identified, by binding of a decoder probe nucleic acid sequence to a complementary sequence termed a decoder binding sequence. In the basic MPSS method, sixteen decoder probes are used to hybridize to the arrayed microbeads in 16 hybridization subcycles, which are all imaged after each subcycle hybridization.

The instant invention may be employed to improve above the MPSS technique described by Brenner et al. (2000), supra. Because each adapter only binds to about ¼ of the beads, the MPSS technique described in the paper only gives about ½ a bit of information at each step. The technique can be improved by using adaptors that each bind a higher proportion of beads, preferably about equal to about ½ of the beads, instead of adaptors that bind to ¼ of the beads. This may be effected by use of adapters having a single sequence position with partially overlapping doubly degenerate base pairing sets. Two adaptors recognizing at a sequence position in the 4 base pair overhang described by Brenner et al., for example, {C, T}, and {A, C} respectively. One of ordinary skill in the art would appreciate that such overlapping degeneracies are obtainable, for example by utilizing overlaps in naturally occurring wobble base pairing known in molecular biology, such as P or dP (Moriyama et al. (1998) *Nucleic Acids Res.* 26(9):2105-11; Brown et al. (1997) *Amersham Life Science News* 23:18-19) and 8-oxo-G or 8-oxo-dG (Pavlov et al. (1994) *Biochemistry* 33:4695-701; Zaccolo et al. (1996) *J. Mol. Biol.* 255:589-603; Brown et al. (1997), supra)

For example, the MPSS adapters taught by Brenner et al., 16 adapter sequences having four nucleotide overhangs (overhang position indicated):

(i) adapter position four (analyte "base 1"):

5'-NNNA, 5'-NNNG, 5'-NNNC, 5'-NNNT;

(ii) adapter position three (analyte "base 2"):

5'-NNAN, 5'-NNGN, 5'-NNCN, 5'-NNTN;

(iii) adapter position two (analyte "base 3"):

5'-NANN, 5'-NGNN, 5'-NCNN, 5'-NTNN;

(iv) adapter position one (analyte "base 4"):

5'-ANNN, 5'-GNNN, 5'-CNNN, 5'-TNNN, where N represents any of A or G or C or T(U).

The sixteen adapter sequences listed above are actually adapter sets, each adapter set having $4^3$ (64) nucleic acid sequences by virtue of N being any of four nucleotides. These sets can be replaced by eight adapter sequence sets having the sequences listed below. Every four adapter sets corresponding to a specific position of interest or variable position can be replaced by a pair of adapter sets and each group of four sequences from these four adapter sets that differ only at one position can be replaced by a pair of overhang sequence adapters. Because the MPSS adapters described by Brenner et al., employ ten nucleotide long sequences to tag or label the adapters termed $F_n$ by the authors, the overhang sequences linked to the $F_n$ sequences by a common 14 nucleotide long linking nucleic acid sequence 5'-ACGAGCTGCCAGTC-3' (SEQ ID NO: 5).

Because each $F_n$ sequence, which is detected in the MPSS method of Brenner et al. by hybridization to one of the 256 $F_n$ decoder binding site sequences, which number 16 unique sequences, four (signifying the four possible nucleotides) for each overhang position, to the complementary phycoerythrin labeled (PE-labeled) decoder probes, which also number 4 for each position (thus 4*4 or 16 unique sequences en toto, and thus 16 adapters, or adapter groups, and PE-labeled decoder probes). For each ligation step of the MPSS method, in which one of the four possible positions is probed or determined, sixteen decoder probes, one for each of the sixteen adapter sequence groups having the overhang sequences depicted above, are hybridized to the decoder binding sites of the encoded adapters in sixteen hybridization cycles, and the arrayed beads are imaged after each such hybridization.

The methods and degenerately base pairing sequences of the instant invention permit halving the number of adapters used and consequently halving the total number of decoder binding sequences and complementary PE-labeled decoder probes, and halving the number of subcycles required to image a ligation cycle and the number of PE-labeled decoder probes per ligation cycle. Using two color labels for decoder probes can reduce the number of subcycles in half again. Additionally possible is the use of partially overlapping unique doubly degenerate sequence positions in the labeled decoder probe sequences to replace four decoder sequences with a pair and further reduce the number of PE-labeled decoder probe sequences directly.

The adapter probe sequences (sequence sets as N is A, T(U), G or C) employed by the method of the instant invention are:

(i) adapter position four (analyte "base 1"):

5'-NNN$\psi_1$, 5'-NNN$\psi_2$;

(ii) adapter position three (analyte "base 2"):

5'-NN$\psi_1$N, 5'-NN$\psi_2$N;

(iii) adapter position two (analyte "base 3"):

5'-N$\psi_1$NN, 5'-N$\psi_2$NN;

(iv) adapter position one (analyte "base 4"):

5'-$\psi_1$NNN, 5'-$\psi_2$NNN

In the preceding sequences, $\psi_1$ represents a position having, for example, the doubly degenerate base pairing set {A, G} and $\psi_2$ position having, for example, the doubly degenerate base pairing set {G, C}. Any of the $\psi_1$, and $\psi_2$ doubly degenerate base pairing sets listed in Table 1 below may be employed for $\psi_1$ and $\psi_2$.

For example $\psi_1$ may have the doubly degenerate base pairing set {A, G}, and $\psi_2$ may have the doubly degenerate base pairing set {A, C}, in which case $\psi_1$ may be dP and $\psi_2$ may be 8-oxo-dG. Alternatively, for $\psi_1$ having the doubly degenerate base pairing set {A, G}, and $\psi_2$ having the doubly degenerate base pairing set {A, C}, $\psi_1$, may be $X_1$ and $\psi_2$ may be $X_2$, $X_1$ being about equal amounts of T and C and $X_2$ being about equal amounts of T and G as described above. Or for the same $\psi_1$ and $\psi_2$ base pairing sets, $\psi_1$ may be $X_1$ and $\psi_2$ may be 8-oxo-dG, or $\psi_1$ may be dP and $\psi_2$ may be $X_2$. Those of ordinary skill in the art will appreciate that to obtain the same signal intensity from hybridization of $X_1$ and $X_2$ type probes as from degenerately pairing nucleotide probes such as those incorporating P or 8-oxo-G, about twice as much probe will be required because only half of the $X_1$ or $X_2$ probe can hybridize to a sequence within the probes complementary set, while substantially all of the dP or 8-oxo-G probe can hybridize to analyte sequence in the respective complementary sets.

If $\psi_1$ has the doubly degenerate base pairing set {A, G}, and $\psi_2$ has the doubly degenerate base pairing set {G, C}, if both $\psi_1$ and $\psi_2$ probes bind, then the analyte nucleic acid sequence position is occupied by G. If the $\psi_1$ probe binds and $\psi_2$ probe does not bind, then the identity of the base at probed position is A, while if the $\psi_2$ probe binds and $\psi_1$ probe does not bind, the identity of the base at probed position is C. If neither probe hybridizes, the identity of the base at the probed position is T. The process is repeated with $\psi_1$ and $\psi_2$ probes for each overhang position (four in all for the instant invention modified MPSS method). If it is desirable to detect a signal for every case, a ninth adaptor, 5'-AAAA, may be included.

Analogously, in the case that $\psi_1$ has the doubly degenerate base pairing set {A, G}, and $\psi_2$ has the doubly degenerate base pairing set {A, C}, e.g. $\psi_1$ is dP and $\psi_2$ is 8-oxo-dG, if both $\psi_1$ and $\psi_2$ probes bind, then the analyte nucleic acid sequence position is occupied by A. If the $\psi_1$ probe binds and $\psi_2$ probe does not bind, then the identity of the base at probed position is G, while if the $\psi_2$ probe binds and $\psi_1$ probe does not bind, the identity of the base at probed position is C. If neither probe hybridizes, the identity of the base at the probed position is again T. The process is repeated with $\psi_1$ and $\psi_2$ probes for each overhang position (four). If it is desirable to detect a signal for every case, a ninth adaptor, 5'-AAAA, may be included.

There are many pairs of partially overlapping doubly degenerate base pairing sets that accomplish substantially the same result. The common element is that they use pairs of hybridization probes that, on the average, hybridize to about ½ of the sequences. In the nine hybridization probe case described above, only eight of the probe sets (of $4^3$ or 64 sequences each) hybridize to half the beads. The ninth only hybridizes to 1/256. There are more complex code makes all nine probes about equal. To do this, each adaptor set must bind to about $4^{4/9}$ combinations. Obviously, similar codes could be constructed for overhangs with other than four. The method can also be applied to multicolored probes, to allow multiple tests to be made simultaneously.

In the MPSS method the adapters are labeled hybridization probes. Other methods such as SBH as described by Drmanac et al. in U.S. Pat. No. 5,525,464, may not require discrete label moieties or even labels intrinsic to the nucleic acid such as $^{32}$P as noted above. Additionally, if a label is required or desired, depending upon the method, the label may be or a discrete moiety linked to or a label intrinsic to analyte sequence, or fragments thereof. For example, if the spatial array on a substrate surface described in U.S. Pat. No. 5,744,305 to Fodor et al., the arrayed nucleotides will be unlabeled hybridization probes incorporating one of a pair of partially overlapping unique doubly degenerate base pairing positions. The analyte sequence fragments, comprising overlapping analyte sequence segments generated, for example, by amplification followed by endonuclease digestion of several fractions with different endonucleases will be labeled, more easily by incorporation of $^{32}$P or the like than by linking a discrete label. Detection of the heat of hybridization by infrared photography can also be employed. The nucleic acid of such an array may be formed in situ or ex situ.

A spatial array on a substrate surface, described in U.S. Pat. No. 5,744,305 to Fodor et al., of analyte sequences could be employed to perform parallel sequencing using hybridization probes that are labeled. To the extent the analyte sequences are long, only the ends should be probed, and successive digestion and hybridization cycles should be performed. For example the MPSS method described by Brenner et al. could be adapted to such a single substrate array using ex situ synthesized analyte sequences obtained by PCR amplification and attached to the discrete predefined regions comprising the array sites by photolithographic methods, and the sequence of adapter ligations and endonuclease digestions may be performed on the entire array. The methods and sequences of the instant invention may be employed to reduce the number of adapters required, with similar advantages. The increase in signal to noise obtainable from the instant invention as described below is more important with such an array than with discrete beads arrayed, because of array site impurity problems, which reduce S/N for photolithographic arrays as a consequence of the photolithographic method.

The methods and sequences of the invention can also be employed for PCR based amplification for detection. Briefly, a mutation from a single base substitution, a mutant single nucleotide polymorphism (SNP) can be detected, in genomic DNA and in cDNA made from mRNA with reverse transcriptase by use of PCR primers having the variable or probe position having one of a pair of the partially overlapping doubly degenerate. The primer/probes are preferably designed so that the known mutant SNP is amplified by both primers and the "normal" (consensus) nucleotide at the position is not amplified at all. In testing a large population, some different SNPs that are either mutations or have no effect on phenotype are likely to be detected as resulting in amplification of one or the other probe. The amplification by both probes for the known mutation enhances certainty of identification.

Quantification of the amplified product can be used for allelic analysis of genomic DNA for SNPs. For example, with probes designed as described in the immediately preceding, if a known mutant SNP is present on both alleles, analysis of genomic DNA will yield twice as much product from each probe, as when the "normal" allele is present on one chromosome and the mutant on the second. Considering a single nucleotide position for two alleles, as there are four bases, sixteen possible combinations exist, but only nine possible pairs exist. Using two primers of the invention having partially overlapping doubly degenerate base pairing sets of the invention, each allele can be amplified by one both or neither primers, for a total of nine possible results, which are distinguishable if the amplified product resulting from each primer is quantified. For Primer 1 (P1) and P2 the following possibilities exist: {(P1: both alleles), (P2: both)}, {(P1: both), (P2: one)}, {(P1: both), (P2: none)}, {(P1: one), (P2: both)}, {(P1: one), (P2: one)}, {(P1: one), (P2: none)}, {(P1: none), (P2: both)}, {(P1: none), (P2: one)}, {(P1: none), (P2: none)}. Thus by quantification of amplification product from genomic DNA using PCR primer/probes and methods of the invention, allelic analysis of a single nucleotide position can be obtained. Those of skill in the art will appreciate that longer probes are less likely to yield false positive amplifications resulting from sequence repeated in the genome but not actually from the alleles of the gene of interest. Thus depending upon how frequently a probed sequence is likely to appear in the genome, the length of the primer can be adjusted. Also cytogenetic methods exist for separating a specific chromosome, such as the two copies of chromosome 21 in the human genome from, the other chromosomes to reduce the possibility of false positive amplifications. Alternatively for transcribed sequence elements, selective expression and cDNA analysis may be used to analyze alleles by the invention. Quantification can be calibrated against known sequence genomic alleles for better calibration of quantification.

As mentioned above, the following 12 pairs of degenerate base pairing sets for $\psi_1$ and $\psi_2$ can be employed, in the preceding sequences, or in longer analogous sequences, with the "Ultimate Check Probe" with the indicated base sequence with the complementary base (base not base pairing with either $\psi_1$ or $\psi_2$) in parentheses. Additional Check Probes having the sequence 5'-NNZN, where Z base pairs with the base represented in neither $\psi_1$ or $\psi_2$ base pairing set, may be employed for each pair of probes such as (5'-NN$\psi_1$N, 5'-NN$\psi_2$N), to decrease errors further, albeit with an additional probe for each two probes each having $\psi_1$ or $\psi_2$ degenerately pairing at one position instead of an additional check probe for the complete set of q pairs of probes for a probed sequence q nucleotides in length. For example q=4 in the preceding sequences, $Z_q$ is the sequence 5'-ZZZZ, representing the Ultimate Check Probe, which ensures that a sequence not hybridizing to any probes in the set of paired degenerately hybridizing probes {(5'-$\psi_1$NNN, 5'-$\psi_2$NNN), (5'-N$\psi_1$NN, 5'-N$\psi_2$NN), (5'-NN$\psi_1$N, 5'-NN$\psi_2$N, (5'-NNN$\psi_1$, 5'-NNN$\psi_2$)}, is actually a nucleic acid sequence. The set of check probes {5'-ZNNN, 5'-NZNN, 5'-NNZN, 5'-NNNZ} may be employed to check each pair of degenerately hybridizing probes, decreasing error at a cost of an increased number of probes.

TABLE I degenerate base pair sets

| $\psi_1$ base pairs with set: | $\psi_2$ base pairs with set: | Check Probes |
|---|---|---|
| A or T | A or C | $C_q$(G), Z = C |
| A or T | A or G | $G_q$(C), Z = G |
| A or T | C or T | $C_q$(G), Z = C |
| A or T | G or T | $G_q$(C), Z = G |
| C or G | A or C | $A_q$(T), Z = A |
| C or G | A or G | $A_q$(T), Z = A |
| C or G | C or T | $T_q$(A), Z = T |
| C or G | G or T | $T_q$(A), Z = T |
| A or C | C or T | $C_q$(G), Z = C |
| A or C | A or G | $A_q$(T), Z = A |
| A or G | G or T | $G_q$(C), Z = G |
| G or T | C or T | $T_q$(A), Z = T |

As indicated, code can be constructed for numbers of bases (q) other than 4.

A note on error rates:

The use of degenerate probes will also increase the is signal to noise ratio, because some of the mismatched bindings (⅓ of the cases) will still result in a correct indication. This is in contrast to the single-nucleotide probe, where all of the misbindings produce noise.

This helps in two ways, by reducing the noise and by increasing the signal. For example assume a specific base pairing interaction. Denoting $S_A$ as the signal from a correct base pairing with the nucleotide A, and $S_T$, $S_G$ and $S_C$ are analogously defined, and denoting $N_{GA}$ as the noise from a mispairing with a nucleotide that is G but is read as A, and $N_{TA}$, $N_{CA}$ and $N_{GA}$ analogously, the signal to noise ratio for detection of A is:

$[S/N](A)=S_A/(N_{TA}+N_{GA}+N_{CA})$. Similarly, for G,C and T, respectively: $[S/N](G)=S_G/(N_{TG}+N_{AG}+N_{CG})$; $[S/N](C)=S_C/(N_{TC}+N_{GC}+N_{AC})$; and $[S/N](T)=S_T/(N_{AT}+N_{GT}+N_{CT})$. These can all be approximated, assuming about equal magnitudes for S values (of "s") and N values (of "n") as $S/N \cong s/3n$. For adapters having the $\psi_1$ or $\psi_2$ doubly degenerate base pairing positions, assume some base pairing sets, e.g., assume that $\psi_1$ is dP (complementarity set: {A,G}) and $\psi_2$ is 8-oxo-dG (set: {C, A}) then: $[S/N](\psi_1)=(S_C+S_T)/(N_{A\psi1}+N_{G\psi1}) \cong s/n$ and $[S/N](\psi_2)=(S_C+S_A)/(N_{T\psi2}+N_{G\psi2}) \cong s/n$. Thus the approximate ratio of improvement in S/N for degenerate detection at a position is $\rho(\psi_1) \cong \rho(\psi_2) \cong (s/n)/(s/3n)=3$. Because determinate use of the doubly degenerate probes requires, assuming no additional "check" probes, at a minimum two measurements at the degenerate S/N for identification of a given nucleotide the net S/N for the conjunction of the two measurements $\rho(\psi_1 1\psi_2) \approx \rho(\psi_1)/2 \approx \rho(\psi_2)/2=3/2$. Note that this S/N enhancement become more significant as the error rate increases for mispairings, for example with longer hybridizing sequences or terminal positions of interest.

This S/N analysis is for detection of pairing, thus any error from the presence of wrong sequence is also more easily detectable by the hybridization probes of the invention. This enhanced detection sensitivity can become problematic in several contexts where the sequence to be detected by hybridization is incorrect or not the intended sequence. For example in the MPSS method of Brenner et al., if the in vitro cloning into the beads is low fidelity, or after a number of ligation and digestion cycles either incomplete endonuclease digestion or spontaneous degradation of the sequences results in exposure of incorrect bases. Thus in contexts where such incorrect sequence may be exposed, resort to non-degenerate base pairing positions may be required. For example, in the MPSS method utilizing the method and sequences of the instant invention, resort to the standard MPSS adapters disclosed by Brenner et al., may be advantageous after a number of cycles to reduce signal enhancement for improperly exposed sequence.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains.

All patents, patent applications, journal articles and other references cited herein are incorporated by reference in their entireties for their disclosure concerning any pertinent information not explicitly included herein.

The following examples are put forth so as to provide those of ordinary skill in the art with a complete disclosure and description of how to implement the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

In these examples, the following abbreviations have the following meanings:

Å=Angstrom (0.1 nm)
C=Centigrade
kg=kilogram
M=Molar
mg=milligram
ml=milliliter
mm=millimeter
N=Normal
nm=nanometers

EXAMPLE 1

Preparation of Nucleic Acid Sequences for MPSS Adapters

Oligonucleotides are either purchased presynthesized from Genetic Designs, Inc. Houston, Tex. or made on an Applied Biosystems 381A DNA synthesizer. All sequences used are purified by HPLC or gel electrophoresis, which may optionally be omitted.

The following adapter sequences are MPSS encoded adapters of the instant invention for reducing the number of encoded adapters required for the MPSS method. The four nucleotide overhangs are indicated in bold and the decoder binding sequence tag or label is underlined. These are connected by the common sequence 5'-ACGAGCTGCCAGTC (SEQ ID NO: 5), and the common sequence is doble stranded, being hybridized to the complementary sequence 5'-GACTGGCAGCTCGA (SEQ ID NO: 6). The adapter sequences are listed in groups based on their probing and coding for different sequence positions corresponding to the overhang position as in the MPSS method in general, with pairs of adapters having positions with doubly degenerate partially overlapping base pairing sets according to the instant invention instead of the four adapters of MPSS practiced without the instant invention. Thus, the adapters include those with doubly degenerate base pairing nucleotides having partially overlapping base pairing sets, and adapters having about equal proportions of two nucleotides at the doubly degenerate base pairing position. The adapters with doubly degenerate base pairing nucleotides having partially overlapping base pairing sets incorporate dP and 8-oxogG because of their appropriate base pairing properties for the practice of the invention and commercial availability, are organized by probed position as follows:

Overhang position 4, analyte base 1:

5'-NNN(dP)ACGAGCTGCCAGTC<u>CATTTAGGCG</u> (SEQ ID NO: 7);

5'-NNN(8-oxo-dG)ACGAGCTGCCAGTC<u>CGCTTTGTAG</u> (SEQ ID NO: 8);

Overhang position 3, analyte base 2:

5'-NN(dP)N ACGAGCTGCCAGTC<u>GGAACCTGAA</u> (SEQ ID NO: 9);

5'-NN(8-oxo-dG)N ACGAGCTGCCAGTC<u>ATTCCTCCTC</u> (SEQ ID NO: 10);

Overhang position 2, analyte base 3:

5'-N(dP)NNACGAGCTGCCAGTC<u>CGAAGAAGTC</u> (SEQ ID NO: 11);

5'-N(8-oxo-dG)NNACGAGCTGCCAGTC<u>GGCGATAACT</u> (SEQ ID NO: 12);

Overhang position 1, analyte base 4:

5'-(dP)NNNACGAGCTGCCAGTC<u>GCATCCATCT</u> (SEQ ID NO: 13);

5'-(8-oxo-dG)NNNACGAGCTGCCAGTC<u>GCCAGTGTTA</u> (SEQ ID NO: 14), where N is A, T(U), G or C.

Also synthesized are the following, grouped by probed position:

Overhang position 4, analyte base 1:

5'-NNN($X_1$)ACGAGCTGCCAGTC<u>CATTTAGGCG</u> (SEQ ID NO: 15);

5'-NNN($X_2$)ACGAGCTGCCAGTC<u>CGCTTTGTAG</u> (SEQ ID NO: 16);

Overhang position 3, analyte base 2:

5'-NN($X_1$)NACGAGCTGCCAGTC<u>GGAACCTGAA</u> (SEQ ID NO: 17);

5'-NN($X_2$)NACGAGCTGCCAGTC<u>ATTCCTCCTC</u> (SEQ ID NO: 18);

Overhang position 2, analyte base 3:

5'-N($X_1$)NNACGAGCTGCCAGTC<u>CGAAGAAGTC</u> (SEQ ID NO: 19);

5'-N($X_2$)NNACGAGCTGCCAGTC<u>GGCGATAACT</u> (SEQ ID NO: 20);

Overhang position 1, analyte base 4:

5'-($X_1$)NNNACGAGCTGCCAGTC<u>GCATCCATCT</u> (SEQ ID NO: 21);

5'-($X_2$)NNNACGAGCTGCCAGTC<u>GCCAGTGTTA</u> (SEQ ID NO: 22), where N N is A, T(U), G or C, and $X_1$ is C or T in equal proportions, and $X_2$ is G or T in substantially equal proportions.

EXAMPLE 2

Preparation of Nucleic Acid Sequences Intrinsically Labeled with $^{32}P$

Labeling of oligonucleotides is performed as described in example one with the standard $^{32}P$ labeled dNTPs: $^{32}P$-DATP, dGTP, dTTP, dCTP (Amersham, Cambridge UK). The doubly degenerately pairing 8-oxo-dG, which pairs with C and A, dP, which pairs with A and are also obtained from Amersham, UK.

EXAMPLE 3

Hybridization Conditions, Thermodynamics of Hybridization, Determination of $T_m$, and Probe Design Wallace et al. (1979) *Nucl. Acids Res.* 6:3543 describe conditions that differentiate the hybridization of 11 to 17 base long oligonucleotide probes that match perfectly and are completely homologous to the target nucleic acid from similar oligonucleotide probes that contain a single internal base pair mismatch. Hybridization stringency refers to differences in hybridization thermodynamics under the applicable conditions permitting distinction between various levels of complementarity, often between a single base mismatch for a certain nucleotide length probe and perfect complementarity therefor. Wood et al. (1985) *Proc. Natl. Acad. Sci.* 82: 1585 describe conditions for hybridization of 11 to 20 base long oligonucleotides using 3M tetramethyl ammonium chloride, $N(CH_3)_4Cl$, wherein the melting point of the hybrid depends only on the length of the oligonucleotide probe, regardless of its GC content. As disclosed in these references 11-mer oligonucleotides are the shortest ones that generally can be hybridized successfully, reliably and reproducibly using known hybridization conditions.

Drmanac et al. describe conditions, and methods for determination of conditions, for reliable hybridizations with oligonucleotides as short as six to eight bases long in U.S. Pat. No. 5,695,940. Such reliable hybridizations may be obtained with probes six to eight nucleotides in length under conditions described in the following. All experiments are performed with a floating plastic sheet providing a film of hybridization solution above the filter, permitting maximal reduction in the amount of probe. The high concentration of sodium lauroyl sarcosine instead of sodium lauroyl sulfate in the phosphate hybridization buffer allows dropping the reaction from room temperature down to 12° C. Similarly, the 4-6×SSC, 10% sodium lauroyl sarcosine buffer allows hybridization at temperatures as low as 2° C. The detergent in these buffers is essential for obtaining tolerable background with up to 40 nM concentrations of labeled probe. Using this method (Drmanac et al. U.S. Pat. No. 5,695,940) characterization of the thermal stability of short oligonucleotide hybrids was determined on a prototype octamer with 50% GC content, i.e. probe of sequence 5'-TGCTCATG. The theoretical expectation is that this probe is among the less stable octamers, in the 50th percentile or below in stability. Its transition enthalpy is similar to those of more stable heptamers and probes as short as 6 nucleotides in length Bresslauer et al. (1986) *Proc. Natl. Acad. Sci. U.S.A.* 83: 3746. The stability of the 8 bp oligonucleotide duplex hybrid as a function of temperature is evidenced: Parameter $T_d$, the temperature at which 50% of the hybrid is melted in unit time of a minute is 18° C. The result shows that $T_d$ is 15° C. lower for the 8 bp hybrid than for an 11 bp duplex (Wallace et al. (1979) *Nucleic Acids Res.* 6: 3543).

Lane et al. describe a method of measuring thermodynamic parameters of hybridization for nucleic acid probe design in U.S. Pat. No. 6,027,884. Absorbance versus temperature profiles (optical melting curves) were collected for each of the molecules at heating and cooling rates of 60° C. per hour over the temperature range from 5 to 85° C. A data point is collected about every 0.1° C. Melting curves for samples are collected as a function of total strand concentration, $C_T$, over a 200 fold range from approximately 500 nM to 100 μM. Absolute absorbance readings ranged from 0.08 OD to 1.3 OD. Optically matched quartz cuvettes with 1 and 0.1 cm path lengths are employed. Such optical nucleic acid melting curves are entirely reversible upon cooling at the same rate. The optical melting curves are normalized to upper and lower baselines and converted to $2_B$ (the fraction of duplex molecules) versus temperature curves. From these curves the melting or transition temperature, $T_m$, was determined as the temperature where $2_B$=0.5. These $2_B$ versus T curves may then be analyzed assuming the transitions occur in an "all-or-none" or "two-state" manner, permitting evaluation of the transition by a van't Hoff plot of $1/T_m$ versus $\ln(C_T)$. The linear equation describing the resulting plot is:

$$1/T_m = (R/H)\ln(C_T) + (S/)H \qquad (1).$$

The slope of the van't Hoff plot yields $-R/\Delta H$ and the intercept provides $\Delta S/\Delta H$. The experimentally determined total free energy is then determined from $\Delta H$ and $\Delta S$ values at 298.15°K by $\Delta G_T = \Delta H - T^* \Delta S$ (2).

Thermodynamic parameters of the melting transitions of hybridized nucleic acids are also measured by differential scanning calorimetry (DSC). A MC-2 (Microcal, Northampton, Mass.) DSC instrument is employed. In preparation for calorimetric melting curve measurements, any protected synthetic DNA samples are deprotected and vacuum dried. Samples are then rehydrated in double distilled (dd) water and dialyzed against dd-water for four days. Upon completion of dialyses samples are vacuum dried and then rehydrated in melting buffer. Samples may be electrophoretically purified as needed, although typically, experiments performed on the same nucleic acid sequence with and without electrophoretic purification are expected to give identical results. Sample and reference buffer solutions are filtered through 0.45:M pore size filters. At least 25 to 100 OD units (absorbance at 260 nm in a 1 cm pathlength cuvette) of DNA solution was melted in the 1.2 ml reaction chamber of the calorimeter. DNA strand concentrations estimated from extinction coefficients determined by the n-n method, vary from about 3 to about 10 mM. These concentrations are 2 to 10 times higher than in the optical melting experiments. Calorimetric data is collected as the change in excess heat capacity at constant pressure, $\Delta Cp$, versus temperature, T. The average buffer base line determined from eight scans of the buffer alone is subtracted from these curves. The calorimetric transition enthalpy, $\Delta H_{cal}$, is determined from the area under the base line corrected $\Delta Cp$ vs. T curve, by the relation: $\Delta H_{cal} = \int \Delta Cp\, dT$ (3). The temperature of the maximum value of the baseline corrected $\Delta Cp$ versus T curve is the transition temperature, $T_m$. The calorimetric transition entropy, $\Delta S_{cal}$, is determined from the baseline corrected $\Delta Cp$ as: $\Delta S_{cal} = \int (\Delta Cp/T)\, dT$ (4). Calorimetric free-energies $\Delta G_{cal}$ are determined from, $\Delta S_{cal}$ and $\Delta H_{cal}$ by $\Delta G_T = \Delta H - T^* \Delta S$ (2). For every DNA sample, several and preferably at least five forward and reverse $\Delta Cp$ vs. T scans should be performed. Values of $\Delta H_{cal}$, $\Delta S_{cal}$ and $\Delta G_{cal}$ are then obtained as averages from multiple experiments. Estimated experimental errors on DSC values historically obtained for non-degenerately complementary nucleotides are no more than +/−3%.

Oligonucleotide probes of the invention, made according to Example 1 above, 11 to 21 nucleotides in length are experimentally hybridized with complementary oligonucleotides and with oligonucleotides that differ by a mismatch at the probed position. The GC content is varied for the of different nucleotide lengths. The probed position is varied between central and asymmetric internal positions, and some terminal probed position nucleotide probes are also constructed, and the duplexes so formed are experimentally characterized for $T_m$ and other thermodynamic parameters of hybridization.

As each probe of the invention generally comprises at the probed position either equal amounts of two more nucleotides, or a degenerately pairing nucleotide analog such as dP, 8-oxo-dG or Inosine (I), which can pair with A, U and C in mRNA-tRNA wobble (G pairing with U and C in wobble) interactions, and is likely similar to 8-oxo-dG, the degenerate fully complementary hybridizations of these probes are expected to have slightly different stabilizations which will affect $T_m$ to an extent dependent upon the hybridization conditions and oligomer length.

Sequences of the invention having one position corresponding to a probed position are constructed with doubly degenerate base pairing sets given in Table 1 and hybridized to sequences perfectly complementary or mismatched at the probed position to the specific $\psi_i$ doubly degenerate base pairing set. Thus, for example, all pairs of 7-mer probes 5'-NNN$\psi_1$NNN and 5'-NNN$\psi_2$NNN indicated by the sets of nucleotides $\psi_1$ and $\psi_2$ given in Table 1 above are constructed, each 7-mer actually representing a group of 7-mers having $4^6$ (4096) sequences (N is one of A T(U) G or C), and experimentally hybridized under the various conditions.

For the probes of the invention wherein $\psi_1$ is dP and $\psi_2$ is 8-oxo-dG, the 4096 7-mer sequences having dP centrally located and the 4096 sequences having 8-oxo-dG centrally located, e.g. at position 4 of 7, correspond respectively to the 5'-NNN$\psi_1$NNN and 5'-NNN$\psi_2$NNN probes. For probes of the instant invention wherein no nucleotide or nucleotide analog (such as dP and 8-oxo-dG) capable of pairing to two nucleotides is incorporated, for example the probes of the invention wherein $\psi_1$ is $X_1$ and $\psi_2$ is $X_2$, the 4096 7-mer sequences having $X_1$ centrally located and the 4096 sequences having $X_2$ centrally located, where $X_1$ and $X_2$ are defined as above ($X_1$ is equal amounts of T and C and $X_2$ is equal amounts of G and T), correspond respectively to the 5'-NNN$\psi_2$NNN and 5'-NNN$\psi_1$NNN probes. Analogously, probes of the type 5'-N$\psi_1$NNNNN and $\psi_i$NNNNNN represent asymmetric internal and terminal probed position probes because the $\psi_i$ position of the probe, corresponding to the probed position, is an asymmetric internal or terminal position respectively.

Each probe using the two possible nucleotides at the probed position is actually a mixture of two hybridizing sequences in about equal proportion, e.g. an $X_1$ probe {1:1}—{5'-GCT(T)CAG, 5'-GCT(C)CAG} is the equivalent of the single sequence probe incorporating the doubly degenerately pairing nucleotide dP, GCT(dP)CAG. Consequently, the stoichiometric equivalent, in terms of hybridization, of the truly doubly degenerate complementarity probes, such as GCT(dP)CAG is twice that of probes comprising mixtures having equal nucleic acid content, e.g. 1M of GCT(dP)CAG is the stoichiometric equivalent for the purposes of hybridization of the "1M" probe, GCT($X_1$) CAG, which is actually a mixture of 1M 5'-GCT(T)CAG and 1M 5'-GCT(C)CAG, and thus 2M in nucleic acid.

For the thermodynamic parameters depending on concentration, stoichiometric equivalents are compared. Each probe is experimentally hybridized to base pair matched sequences at all positions other than the probed position, with the probed hybridizing sequences comprising any of the standard nucleotides A, T(U), G, C. Thus each of the pair of probes 5'-GCT($\psi_i$)CAG is hybridized experimentally with: 5'-GCT(T) CAG; 5'-GCT(C)CAG; and 5'-GCT(A)CAG; and 5'-GCT(C) CAG. As $\psi_i$ probes that are specified in Table 1 are doubly degenerate, there will be two experimental hybridizations that match at the probed position, these being perfect sequence complementarity, and two hybridizations that mismatch at the probed position, these being single mismatch complementarity. Ideally, a large difference in $T_m$ will exist between the single mismatch and perfect sequence complementarity experimental hybridizations, representing a large thermodynamic destabilization under the applicable conditions, thus permitting an identifiable distinction to be made between a match and mismatch at the probed position. In addition to varying the conditions to alter the mismatch destabilization magnitude, conditions that affect the total stabilization from hybridization, such as amount of tetramethylammonium chloride for a GC rich probe, or probe length of the can be varied to decrease or increase total stabilization. Varying the total stabilization, affects the relative amount of the destabilization from the mismatch, reflected in an increased or decreased $T_m$ depression from the mismatch (corresponding to increased or decreased magnitude of )$T_m$). Typically, probe lengths will be shortened and the effects of GC content negated to increase the relative effect of the mismatch and increase stringency. Note that the $T_m$ and )$T_m$ values will depend on the specific sequences participating in hybridization because the thermodynamic parameters for each of the four experimental hybridizations of a specific probe will actually be different. For the purposes of this example )$T_m$ of, for example a dP::A mismatch or a dP::G mismatch is defined in terms of the mean $T_m$ of the perfect match dP::C and dP::T, and the corresponding thermodynamic parameters ( )[)G], )[)H], and )[)S]), are correspondingly defined. Mismatches for a specific probe having a doubly degenerate position, must be sufficiently relatively destabilized thermodynamically to create a relatively large magnitude negative )$T_m$, and differences in )$T_m$ between mismatches, e.g. a difference in )$T_m$ for a dP::T mismatch, )[dP:mm:T]$T_m$, compared to )[dP:mm:C]$T_m$, and the corresponding thermodynamic functions ( )[dP:mm:T][)G], )[dP:mm:T][)H], and )[dP:mm:T] [)S], and )[dP:mm:C][)G], )[dP:mm:C][)H], and )[dP:mm:C][)S]), are not critical so long as they are sufficient in magnitude to permit appropriate stringency of distinction between perfect and single mismatch complementarity.

In addition to differences between individual mismatches, differences will exist in $T_m$ between probes matching at the position corresponding to the probed position and thus perfectly complementary. The difference in $T_m$ between perfectly matching hybridizations of a doubly degenerate complementarity probe and the two complementary sequences thereto, denoted )$T_m[C_2, C_1]$, must be sufficiently small to not only be substantially smaller than both )[Θ:mm:N]$T_m$ to permit differentiation between single mismatch and perfect complementarity hybridizations, but to reflect sufficiently similar )G of hybridization so that the equilibria for the two matched hybridizations for the doubly degenerately pairing probe yield signals of equivalent intensity, especially for semiquantitative hybridizations, even if completely separate hybridizations are employed. As the probes of the invention, even when each probe is employed separately from the pair, will preferably be contacted with a plurality of analyte sequences simultaneously, as in adapted MPSS, classical array SBH, and potentially in allelic analysis by PCR, all described in the following examples, differences in equilibria must be minimized to reduce differences in intensities and thus competitive effects between two valid signals. Also, with quantitated PCR techniques using the invention sequences as primers, $T_m$ differences that are not so significant to preclude a consensus thermal temperature cycle permitting amplification of both sequences complementary to a doubly degenerately pairing probe can affect relative amplification kinetics, skewing the amplification product towards one of the doubly degenerate amplifications. When pairs of doubly degenerate probes are used with two-color hybridizations, or simultaneously used for PCR, the thermodynamic stabilizations and $T_m$ values as compared between the pair must also be adequately close to effect about equal color signals or amplification quantity, respectively. For $X_1$ type probes the thermodynamics of hybridization must be studied as a probe (a mixture of sequences that hybridize) of stoichiometrically equivalent hybridization capacity, and the individual hybridizing sequences comprising the $X_1$ type or "mixture" probe should be studied. Thus, to evaluate a specific probe pair for a two color assay for employment of such a probe, for example a pair based on $\psi_1$ being $X_1$ and $\psi_2$ being 8-oxo-dG, thermodynamic analysis should be performed on both in amounts that are stoichiometric equivalents in terms of hybridization capacity. Also, the individual hybridizing sequences comprising the $X_1$ probe should be studied separately, to help determine effects of total nucleic acid concentration on hybridization conditions, e.g. both the sequences having at the $\psi_1$ position T and C respectively should be studied separately.

Performing the thermodynamic analyses of this example under different conditions for different types of probe designs (length, symmetry about probed position, etc.), permits identification of probe designs and conditions permitting all the exemplified uses of the instant invention described herein.

EXAMPLE 4

Preparation of LEAE Labeled Detection Probes

Longer emission acridinium ester N-hydroxy succinamide (LEAE-NHS) and its analogs are disclosed by Law et al. in U.S. Pat. No. 5,395,792. These compounds emit light having an intensity maximum at the wavelength 520 nm ($\lambda_{max}$=520 nm). The conjugation of LEAE-NHS to specific decoder probes of Example 1 probe at the 5' end is described below. These longer emission acridinium esters emit at higher wavelength and consequently lower frequency than the DMAE compounds described in the following example, permitting the two chemiluminescent probes to be employed for a two color detection. Specifically, the LEAE chemiluminescent probe is used with decoder probe sequence complementary to decoder binding sites for those adapters of Example 1 having overhang sequences with a sequence position occupied by dP or $X_1$, e.g. having the doubly degenerate base pairing complementarity set: {A, G}. The decoder binding sequences follow: 5'-CATTTAGGCG (SEQ ID NO: 23); 5'-GGAACCTGAA (SEQ ID NO: 24); 5'-CGAAGAAGTC (SEQ ID NO: 25); 5'-GCATCCATCT (SEQ ID NO: 26). The corresponding complementary decoder probe sequences (italics) are consequently: 5'-CGCCTAAATG (SEQ ID NO: 27); 5'-TTCAGGTTCC (SEQ ID NO: 28); 5'-GACTTCTTCG (SEQ ID NO: 29); 5'-AGATGGATGC (SEQ ID NO: 30).

Oligonucleotide 5'-CGCCTAAATG (SEQ ID NO: 27), which has a 5' amino linker, (20 nmoles) in 0.15 ml of water Is treated at room temperature under nitrogen with 0.15 ml of 0.2 M carbonate buffer, pH 8.5 and 0.45 ml of N,N-dimethylformamide (DMF) to give a homogenous solution. To this solution Is added a total of 1.9 mg (3.0 µmoles) of LEAE-NHS in 0.15 ml of DMF in three equal portions, each in a one hour interval. After the addition of the final portion of the LEAE-NHS, the solution was protected from light and stirred at room temperature overnight. The solution was then treated with 2 ml of water and centrifuged at 13,000 RPM for 5 minutes.

The supernatant is passed through a Sepahadex G-25 column (1×40 cm), eluted with water. The very first peak was collected and concentrated in a rotary evaporator at temperature below 35° C. The concentrate is separated on a reverse-phase HPLC column (Brownlee, C-8, RP-300, 4.6×250 mm), eluted with solvent gradient: 5 to 25% B for 15 minutes, followed by 25 to 35% B for 15 minutes, 35 to 60% B for 10 minutes and 60 to 100% B for 5 minutes (A: 0.1 M Et$_3$NHOAc, pH 7.26; B: acetonitrile). The peak with the retention time of ~34.6 minutes was collected and lyophilized to dryness to give 1.43 nmoles of 3'-LEAE-5'-CGC-CTAAATG (SEQ ID NO: 27) probe as determined from its UV absorbance at 260 nm. The probe was stored in 0.8 ml of 50 mM phosphate buffer, pH 6.0 containing 0.1% Bovine Serum Albumin (BSA) at −20° C. before use.

Oligonucleotides 5'-TTCAGGTTCC (SEQ ID NO: 28), 5'-GACTTCTTCG (SEQ ID NO: 29) and 5'-AGATGGATGC (SEQ ID NO: 30), all having an amino linker at the 3' end, are labeled with LEAE at the 3' end in the manner described above.

EXAMPLE 5

Preparation of DMAE Labeled Detection Probes

Dimethyl acridinium esters (DMAE) are disclosed by Law et al. in U.S. Pat. No. 4,745,181. These compounds emit light having an intensity maximum at the wavelength of 430 nm ($\lambda_{max}$=430 nm).

In conjunction with the two color scheme described above and in Example 6 adapters of Example 1 for MPSS sequencing using the methods and sequences of the instant invention are encoded with nucleic acid sequence for decoder binding. The DMAE is linked only to those decoder probes having complementary sequence to decoder binding sequence of those adapters with overhang sequences that incorporate either 8-oxo-dG or $X_2$, such positions having a doubly degenerate base pairing set: {A, C}. The decoder binding sequences follow: 5'-CGCTTTGTAG (SEQ ID NO: 31); 5'-ATTCCTCCTC (SEQ ID NO: 32); 5'-GGCGATAACT (SEQ ID NO: 33); 5'-GCCAGTGTTA (SEQ ID NO: 34). The corresponding complementary decoder probe sequences (italics) are consequently: 5'-CTACAAAGCG (SEQ ID NO: 35); 5'-GAGGAGGAAT (SEQ ID NO: 36); 5'-AGTTATCGCC (SEQ ID NO: 37); 5'-TAACACTGGC (SEQ ID NO: 38).

The oligonucleotide, 5'-CTACAAAGCG (SEQ ID NO: 35) (8.5=moles), Is treated with triethylamine (536 umoles) for three hours at room temperature.

The DMAE-CO$_2$H was activated via mixed anhydride methods disclosed by Law et al. in U.S. Pat. No. 5,622,825, as follows.

DMAE-CO$_2$H (2.5 mg, 5.36 µmoles) is dissolved in 1.5 ml of DMF and chilled in ice for several minutes. Triethylamine (6 µl, 42.9 µmoles) is added, followed by ethyl chloroformate (2.56 µl, 26.8 mmoles) and stirred, chilled, for half an hour. The reaction mixture is then dried with a rotary evaporator.

The residue is dissolved in DMF and the resulting activated DMAE-CO$_2$H (850 nmoles) added to the oligonucleotide, in a total volume of 300 µl of 1:1 DMF:H$_2$O. It is stirred at room temperature overnight.

The reaction mixture is passed through Sephadex G25 (fine) and eluted with water. The first peak was collected, concentrated by rotary evaporation and further purified by HPLC: (Column: Aquapore C8, RP-300,4.6 mm×25 cm (Rainin, Woburn, Mass.); Solvents: solvent A: 0.1 M Et$_3$NHOAc pH 7.2-7.4, solvent B: Acetonitrile; Gradient: (Linear) 8% to 20% B over 20 minutes, to 60% B over 20 minutes; Flowrate: 1 ml/minute; Detection $\lambda$: 254 nm). A product peak is collected and lyophilized to give 329 pmoles of the conjugate. The product is stored in 800 µl of 50 mM PO$_4$, pH 6.0, 0.1% BSA, at −20° C. prior to use. Oligonucleotides 5'-GAGGAGGAAT (SEQ ID NO: 36); 5'-AGTTATCGCC (SEQ ID NO: 37); 5'-TAACACTGGC (SEQ ID NO: 38) are labeled with DMAE at the 3' end in the manner described above.

EXAMPLE 6

Two-Color MPSS with a Microbead Array

The MPSS ligation based sequencing method of Brenner et al. (2000), supra, is described in detail above. The sequences and methods of the instant invention are adapted to the MPSS method by employing the adapter sequences of Example 1 above and the two color decoder probe scheme for these adapters of Examples 4 and 5 above to the MPSS method.

The sequences are in vitro cloned onto the beads so that there are about $10^4$-$10^5$ identical sequences per bead, and digestion is by the endonuclease BbvI. Each cycle after the initial cleavage with DpnII and fill in is summarized as follows: (i) ligation; (ii) detection by hybridization of decoder probes to decoder binding sites; (iii) BbvI digestion. In the MPSS method without the instant invention, sixteen decoder binding sequences and decoder probes exist, which require sixteen cycles of decoder hybridizations to completely image the arrayed beads. As the methods and sequences of the instant invention reduce the number of adapters, decoder binding sequences and decoder probes to eight.

Use of decoder probes comprising only the sequences of the eight decoder probe sequences (SEQ ID NOS 27-30, 35-38) intrinsically labeled with $^{32}$P as described in Example 2 above eight cycles may be used to completely image the signatures for each ligation/imaging/cleavage cycle.

Use of the two color chemiluminescent decoder probe labeling system of Examples 4 and 5 permits only imaging hybridization four subcycles per one ligation cycle.

EXAMPLE 7

Two-Color MPSS Using Planar Spatial Substrate Surface Array

An array of the type described by Fodor et al in U.S. Pat. No. 5,744,305 is constructed by, methods disclosed therein, preferably by presynthesizing oligonucleotides to be sequenced in parallel. In situ synthetic methods may be substituted with the caveat that the resulting array site regions will then not have as pure a population of the polymer intended for synthesis at the site. These consequently preferably ex situ made oligonucleotides are attached by now widely known phosphoramidite chemistry adapted to photolithographic methods, e.g., by photolabile protecting groups used for masking. The array is constructed at a density of about 100 to 1,000,000 sites per cm$^2$, preferably at a density of about 1,000 to 100,000 sites per cm$^2$. All other aspects are as described in Example 6. The optional employment of the two colour visualization method permits streamlining the process so that only four decoder hybridization subcycles are required for complete imaging each ligation cycle.

EXAMPLE 8

Classical SBH

The arrays of the type described in the preceding example can be adapted to perform the classical SBH. Instead of arraying analyte sequences, analysis of the types of sequences to be sequenced is performed by heuristic methods using bioinformatics and data specific to the species and type of DNA to be sequences. The SBH methods of Drmanac et al. (U.S. Pat. No. 5,525,464) are described in more detail above. Analyte sequences are generated by PCR amplification with the $^{32}$P labeling of Example 2 by use of the radioisotopically labeled dNTPs.

After analysis to determine the proper value of N, the length of the arrayed probes, and the proper length of the analyte fragments, the array is constructed. Instead of an array of all possible N-mers, a pair of N-mers each having a position with a unique partially overlapping doubly degenerate base pairing set is substituted for four possible N-mers having the standard nucleotides. Thus, for 8-mers, instead of four array sites having:

5'-NNNN(A)NNN;

5'-NNNN(T)NNN;

5'-NNNN(G)NNN;

5'-NNNN(C)NNN, two array sites are substituted.

The substituted two sites have the following probe sequences:

5'-NNNN(dP)NNN;

5'-NNNN(8-oxo-dG)NNN.

Alternatively the two sites substituted for the four are ($X_1$ and $X_2$ defined as above):

5'-NNNN($X_1$)NNN;

5'-NNNN($X_2$)NNN.

Or with adjustment of the density of polymers (NOT SITE DENSITY) to be twice as much for $X_1$ or $X_2$ compared to dP and 8-oxo-dG both the following are alternatively possible:

5'-NNNN(dP)NNN;

5'-NNNN($X_2$)NNN; or

5'-NNNN($X_1$) NNN;

5'-NNNN(8-oxo-dG)NNN.

Radioisotopically labeled analyte fragments may be visualized autoradiographically, or infrared photographic methods may be employed with unlabeled analyte fragments. Two analyte fragments could be simultaneously sequenced by two color methods employing the chemiluminescent labels of Examples 4 and 5.

EXAMPLE 9

Allelic Analysis for Canavan Disease by PCR of Genomic DNA Using Primer Sequences and Methods of the Invention Canavan disease is an autosomal recessive disorder caused by aspartoacylase deficiency consequent accumulation of N-acetylaspartic acid in the brain. An A to C base change in nucleotide 854 of the open reading frame (ORF) of the human gene nucleic acid sequence, corresponding to nucleotide 1012 of the 1435 base pair long mRNA reverse transcribed cDNA, causing a missense mutation of amino acid 285 from glutamine (Glu) to alanine (Ala), has been shown to cause Canavan disease in the majority of alleles for the disease, with other mutations identified, as taught in U.S. Pat. No. 5,697,635 to Matalon et al. Another mutation causing the disease is an ORF 693 mutation of C to A, resulting in the codon change TAC to TAA and a consequent termination instead of incorporation of Tyr 231. Yet another allele which has been identified is an ORF 914 position C to A change, causing the codon change of GCA to GAA for amino acid 305 in aspartoacylase, resulting in the missense mutation substituting a Glu (glutamic acid) for Ala 305.

An allelic analysis of genomic DNA by PCR, or of chromosome 17, easily separated by cytogenetic manipulative techniques, may be devised for either point mutation. The PCR amplification technique (see, for example, Mullis et al., U.S. Pat. No. 4,683,202) and its requirements are widely appreciated. The mutation is detectable by dP and 8-oxo-dG probes comprising PCR primers of the invention, with the doubly degenerate base pairing nucleotides at the positions corresponding to, and pairing with, the probed-for mutation. An allelic analysis of the most prevalent A to C mutation of nucleotide 854 of the human aspartoacylase sequence is detectable by a pair of primers having dP and 8-oxo-dG incorporated in a sequence of about fifteen to twenty-five nucleotides, complementary to the sense strand of the human aspartoacylase DNA sequence centered about ORF nucleotide 854. The primer is centered about the probed nucleotide position, as internal base pairing mismatches are widely appreciated to be more destabilized than terminal mismatches, although asymmetric internal mismatches are more destabilizing, both reflected in reduction of melting temperature ($T_m$) of hybrids. Longer sequences are more stabilized by hybridization in general, thus less affected by destabilizing mismatches. Such hybridization destabilization reduces the likelihood that primers will hybridize to sequences not having the correct set of nucleotides, e.g. those of the base pairing set, for the specific primer, and thereby decreasing mis-amplifications. Because of the mechanics of the PCR process, in which the primers are lengthened by the action of the polymerase at their 3' in the 5' to 3' polymerization, a mismatch towards the 3' end of the primer is most likely to prevent polymerization should hybridization occur. Thus, for a given primer length, asymmetric internal probe position favors higher stringency of hybridization and asymmetry, and having the probed position towards the 3' end of the primer increases stringency of polymerization. Thus, those of skill in the art will apprehend that the probes discussed below can be adjusted for overall reaction stringency (encompassing both stringency of hybridization and polymerization) and optimization of $T_m$ for the PCR temperature cycling, by adjusting overall length and varying the position of the probed position in the probe-primer sequence.

The symmetric 21 base long primers discussed below can thus be adjusted in length and position of the probed position in the primer-probe sequence to optimize overall stringency and $T_m$ for cycling purposes. Additionally, the degenerately hybridizing probes should have $T_m$ values that differ for hybridization to the different sequences of their complementarity set, insubstantially, and cooling cycles must be at a temperature below the lowest $T_m$ while heating cycles must be at a temperature at least above the higher, and if more than one probe is used simultaneously the heating and cooling cycles need be adjusted, respectively, for the highest $T_m$ and lowest $T_m$ in the system. Generally longer probes and probe pairs of the invention will have closer $T_m$ values for hybridizing with different sequences, both for the same probe and compared with the pairing probe.

The sequence of the non-mutated sense strand of the human aspartoacylase gene beginning with ORF nucleotide 844 (1002 of the 1435 bp cDNA sequence) and ending in nucleotide 864 (1022 of the 1435 bp cDNA sequence) is 5'-TTTGTGAATGAGGCCGCATAT (SEQ ID NO: 39) (probed position bold underlined). This 21 base nucleotide sequence symmetric about ORF nucleotide 854 is complementary to 5'-ATATGCGGCCTCATTCACAAA (SEQ ID NO: 40).

The primers of the instant invention for allelic analysis are pairs of the complementary sequence, 5'-ATATGCGGCCTCATTCACAAA (SEQ ID NO: 40), with the probed position comprising doubly degenerate base pairing sets that partially overlap, e.g. 5'-ATATGCGGCC($\psi_i$)CATTCACAAA (SEQ ID NO: 41), $\psi_i$, indicating either $\psi_1$ and $\psi_2$. Any of the partially overlapping $\psi_1$ and $\psi_2$ sets of Table 1 may be employed, ideally so that the mutation is amplified by both probes and the normal sequence is not amplified at all. The dP based primer, 5'-ATATGCGGCC(dP)CATTCACAAA (SEQ ID NO: 42), and 8-oxo-dG based primer, 5'-ATATGCGGCC(8-oxo-dG)CATTCACAAA (SEQ ID NO: 43), will amplify both the mutant and normal sequences of the A to C mutation of ORF base 854, while only the dG based primer will amplify the ORF 854 mutant (ORF 854=C). Thus the afflicted homozygous mutated individual will exhibit amplification of both alleles by one probe, relative magnitude for simultaneous amplification 1+1=2, the carrier will exhibit amplification of the mutant allele by one primer and amplification of the non-mutated allele by both primers, relative magnitude 2+1=3, and the homozygous non-mutated individual will exhibit amplification of both alleles by both probes, relative magnitude 2+2=4. Thus, the three possibilities can be distinguished by quantifying the amplification product from simultaneous amplification using a combination of probes according to the invention. With $X_1$ and $X_2$ as defined above the, $X_1=\Psi_1$ and $X_2=\Psi_2$ based primer probes, 5'-ATATGCGGCC($X_1$)CATTCACAAA (SEQ ID NO: 44), and 8-oxo-dG based primer, 5'-ATATGCGGCC($X_2$)CATTCACAAA) (SEQ ID NO: 45) will function equivalently to the corresponding dP($X_1$) or 8-oxo-dG ($X_2$) if their levels are doubled to effect the same effective number of primers for each base pairing of the degenerate set, and these may be substituted for one or both of the dP and 8-oxo-dG based primers. Note that, as defined, $X_1$ based primers incorporate about equal amounts of C and T at the probed position and $X_2$ based primers incorporate about equal amounts of G and T. Thus the 5'-ATATGCGGCC($X_1$)CATTCACAAA (SEQ ID NO: 44) primer is actually a mixture of about equal amounts of:

5'-ATATGCGGCC<u>C</u>CATTCACAAA (SEQ ID NO: 46); and

5'-ATATGCGGCC<u>T</u>CATTCACAAA) (SEQ ID NO: 40).

The primer 5'-ATATGCGGCC($X_2$)CATTCACAAA (SEQ ID NO: 45) is actually a mixture of about equal amounts of:

5'-ATATGCGGCC<u>G</u>CATTCACAAA (SEQ ID NO: 47); and

5'-ATATGCGGCC<u>T</u>CATTCACAAA (SEQ ID NO: 40).

Generally, more complicated potential allelic patterns, for example four possible nucleotides at the probed position, may be discerned by quantified amplification with the two primer probes separately, as described above. Except for in utero testing using {dP or $X_1=\psi_1$} and {8-oxo-dG or $X_2=\psi_2$} probes, which must identify the affected genotype, testing of adults for carrier screening in practice involves identifying reduced amplification product from quantitative simultaneous PCR with both primers. Known normal amplifications may be performed for calibration; the possibility of amplifying similar sequences from different genes is reduced by assaying only chromosome 17 pairs from the individual. Analogous primer pairs having the same partially overlapping doubly degenerate base pairing sets at the probed position can be employed for the other Canavan mutations described above for either simultaneous amplification of genomic DNA by both primers of the pair or separate amplification assays where the data is integrated after amplification. Individual chromosomes carrying the allele of interest can be separated to obtain more information, in some cases. In the Canavan context, separating the pair of chromosome 17 in the diploid somatic genome permits multiple primer pairs to be used to simultaneously screen the allele for several different amplification products that can be quantitatively distinguished for more detailed analysis, revealing some of the more rare mutations. Also, as will be appreciated by those skilled in the art is that these primers can also be used for screening based on cDNA derived from reverse transcription of expressed mRNA for the Canavan mutation. One important requirement for the operation of these primers with genomic DNA is that the DS primer sequence (e.g. a DS mutation centered sequence), may not be separated in the genomic DNA by untranslated intron sequence, which is spliced out in post-transcriptional processing. Thus, the probed position of the genomic DNA, for assays employing the cDNA sequence, must not be so close to the splice junction that the sequence of the cDNA is not appropriate for the probe as some spliced out sequence is adjacent the probed position in the genomic DNA. The 854 ORF position mutation at 1012 of the 1435 base pair cDNA sequence of aspartoacylase is far from any intron exon junctions, being about in the middle of Exon 6 of the aspartoacylase gene which corresponds to positions 745 to 1270 of the 1435 base cDNA sequence (ORF 687-1112). For primer design for genomic DNA analysis of mutations near intron exon junctions, some of the mutation adjacent intron sequence must be known. The ORF 693 C to A mutation, for example, is close enough to the beginning of Exon 6 (ORF 687), that design of the primers of the invention for probing this position in genomic DNA is properly designed based in part upon the intron sequence preceding the beginning of Exon 6 (Intron 5 of the aspartoacylase gene), and primers for amplifying cDNA would be necessarily different than primers probing genomic sequence for this mutation (ORF 687 C to A).

A primer pair can be designed for the most common ORF 854 A to C mutation that causes Canavan disease, whereby the mutation sequence is amplified by both primers and the non-mutated sequence is not amplified at all. This would require doubly degenerate partially overlapping base pairing sets at the probed position that both include C as the common nucleotide in the base pairing set with A excluded from both base pairing sets: {C, T}; and {C, G}. Note that $Q_1$, defined as about equal occupancy in the probed position of the bases A and G, has the first of the preceding base pairing sets, and $Q_2$, about equal occupancy of bases G and C, will perform this function. The probe pair for the ORF 854 mutation is thus:

5'-ATATGCGGCC($Q_1$)CATTCACAAA (SEQ ID NO: 48); and

5'-ATATGCGGCC($Q_2$)CATTCACAAA) (SEQ ID NO: 49).

Again, the 5'-ATATGCGGCC($Q_1$)CATTCACAAA (SEQ ID NO: 48) primer is actually a mixture of about equal amounts of:

5'-ATATGCGGCC<u>A</u>CATTCACAAA (SEQ ID NO: 50); and

5'-ATATGCGGCC<u>G</u>CATTCACAAA (SEQ ID NO: 47).

The primer 5'-ATATGCGGCC($Q_2$)CATTCACAAA (SEQ ID NO: 49) is actually a mixture of about equal amounts of:

5'-ATATGCGGCC<u>G</u>CATTCACAAA (SEQ ID NO: 47); and

5'-ATATGCGGCC<u>C</u>CATTCACAAA (SEQ ID NO: 46).

The corresponding base pairing sets of this $Q_i$ based primer pair are listed in Table 1 above. For screening of Canavan alleles from genomic DNA, the mutated homozygous ORF 854 will exhibit amplification of both alleles by both primers for a relative magnitude of 2+2=4. The heterozygous carrier of this ORF 854 mutation will exhibit amplification of one allele by both primers, for a relative magnitude of amplification product of 2+0=2. The homozygous non-mutated ORF 854 individual will exhibit no amplification. Heterozygous mutated individuals with Canavan disease will also exhibit a relative magnitude of 2 for ORF 854 A to C probed amplification product. In practice quantification of PCR product is only required to discern homozygous ORF 854 A to C mutants from carriers in utero, and the $Q_i$ based primer pair may be employed to screen for carriers on the basis of detectible amplification product, with homozygous individuals having A at ORF position 854 not exhibiting any amplification product. Primer pairs can be designed so that the probed-for mutation results in amplification product from both primers and the non-mutated sequence results in no amplification product from either probe. Mixtures of such probe pairs for simultaneous amplification of genomic DNA or expressed cDNA can then be used with quantification of specific sequences amplified by routine methods, for identifying carriers of more exotic mutants and for in utero testing to identify disease in utero from possible heterozygous mutants.

EXAMPLE 10

Allelic Analysis for Canavan Disease by PCR of Genomic DNA Using Arrayed Probe Sequences and Methods of the Invention The sequences described as probes in Example 9 may also be arrayed on separate beads or on an integrated type array having predefined sites as described in U.S. Pat. No. 5,744,305 to Fodor et al., although high densities as described therein are not likely to be required in practice, but higher densities can enhance the analysis by providing more duplication. The PCR primers described by Matalon et al. in U.S. Pat. No. 5,697,635 for specifically amplifying aspartoacylase genomic or cDNA (in its entirety rather than starting inside the coding sequence, as results from employment of the primers of Example 9) may be employed.

Briefly, the pairs of probes having doubly degenerate partially overlapping base pairing sequence positions for identifying different Canavan mutations are attached to sites of an array. The number of probes that must be employed is not reduced for mutations such as the 854 ORF A to C mutation most common in Canavan disease, but if, for example, a mutation of A to a different nucleotide than C at ORF was discovered to cause disease, the number of probes employed could be reduced by use of probes of the instant invention. However, enhancement of the S/N ratio as described above can be obtained advantageously. Again the most convenient approach is to construct the probe pairs so that both hybridize to the mutant sequence and neither hybridizes to the non-mutated probed position sequence. As array sites are separate, and the identity of the probe resident at each site is knowable or predefined, the probe that hybridizes is known without identifying the specific amplified sequence as required for PCR using mixtures of probe pairs. The hybridization to the array is at least semiquantitative, as measured by detecting relative amounts of radioactivity or chemiluminescence as with intrinsically $^{32}P$ labeled or discrete moiety chemiluminescent labeled PCR amplification products. Another semiquantitative measure of hybridization to array sites can be obtained by use of infrared photography. Probe pairs for all known mutations would be incorporated into the array. Such genetic screening arrays incorporating conventional probe sequences appropriate for screening for various Canavan mutations are taught by Shuber et al. in U.S. Pat. No. 5,834,181.

To adapt the sequences and methods of the instant invention to a genetic screening array of the type taught by Shuber et al. in U.S. Pat. No. 5,834,181, a probe pair of the instant invention is substituted for the probes in the Shuber array for each mutation described by Matalon et al. in U.S. Pat. No. 5,697,635, and additional array site pairs can be added for newly discovered mutations. In addition to S/N enhancement, the probe pairs of the instant invention will permit atypical mutations to be detected without construction of specific probes for them. For example, the hypothetical 854 ORF mutation of A to a nucleotide other than C would be detected by use of such an array and the identity of that nucleotide could be discerned thereby.

Those of skill will appreciate that the screening of Example 9 is obtained by the PCR amplification directly, while the use of spatially arrayed sequences positions having doubly degenerate partially overlapping base pairing sets requires a separate PCR amplification step prior to screening. This added step can provide additional information that may make the screening array approach better suited for certain experiments, depending upon the disease, number and type of mutations and the purpose of screening, including whether genotype or phenotype is screened and whether novel SNPs, both mutant and non-mutant are desired to be detected. In the Canavan context, the array method may be preferable for in utero diagnosis of the affected heterozygous mutants, and for screening the general population for carriers with the hope of discovering new single nucleotide polymorphisms at the probed positions, both pathologic (mutant) and non-pathologic.

Thus, an optimal probe pair for the 854 ORF mutation in such an array is:

5'-ATATGCGGCCACATTCACAAA (SEQ ID NO: 48); and

5'-ATATGCGGCCGCATTCACAAA, (SEQ ID NO: 49) with $Q_1$ and $Q_2$ defined as in Example 9.

Again, the 5'-ATATGCGGCC($Q_1$)CATTCACAAA (SEQ ID NO: 48) primer is actually a mixture of about equal amounts of:

5'-ATATGCGGCCACATTCACAAA (SEQ ID NO: 50); and

5'-ATATGCGGCCGCATTCACAAA (SEQ ID NO: 47).

The primer 5'-ATATGCGGCC($Q_2$)CATTCACAAA (SEQ ID NO: 49) is actually a mixture of about equal amounts of:

5'-ATATGCGGCCGCATTCACAAA (SEQ ID NO: 47); and

5'-ATATGCGGCCCCATTCACAAA (SEQ ID NO: 46). The other probe pairs are readily obtained analogously.

I claim:

1. A method of determining the identity of an unknown nucleotide at a position of interest on a target nucleic acid analyte comprising: contacting the target nucleic acid analyte under hybridizing conditions with at least two non-identical oligonucleotide probes having a variable position nucleotide, wherein the variable position nucleotide of at least one of the at least two oligonucleotide probes is a nucleotide that will base pair with at least two nucleotides, the variable position nucleotide of at least one other of the at least two oligonucleotide probes is either a nucleotide that will base pair with at least two nucleotides or a nucleotide incapable of degenerate base pairing, wherein the nucleotides in the variable positions of the at least two oligonucleotide probes collectively base pair with all but one nucleotide; wherein the hybridizing conditions are sufficient to permit the at least two oligonucleotide probes to hybridize to the target nucleic acid analyte when the nucleotide occupying the variable position base pairs with the nucleotide occupying the position of interest, and do not permit the at least two oligonucleotide probes to hybridize to the target nucleic acid analyte when the nucleotide occupying the variable position does not base pair with the nucleotide occupying the position of interest; and wherein the identity of the position of interest is determined by comparing the variable positions of any hybridized oligonucleotide probes for complementarity and the variable positions of any nonhybridized oligonucleotide probes for lack of complementarity.

2. The method of claim 1, wherein four nucleotides are possible at the position of interest.

3. The method of claim 2, wherein the nucleotides for the position of interest are G, T, A and C if the target nucleic acid analyte is DNA; or G, U, A or C if the target nucleic acid analyte is RNA.

4. The method of claim 3, comprising contacting the target nucleic acid analyte under hybridizing conditions with two oligonucleotide probes.

5. The method of claim 4, wherein the nucleotides occupying the variable positions of the two oligonucleotide probes are doubly degenerate.

6. The method of claim 5, wherein the variable position nucleotide of one of the two oligonucleotide probes is dP.

7. The method of claim 5, wherein the variable position nucleotide of one of the two oligonucleotide probes is 8-oxo-dG.

8. The method of claim 5, wherein the variable position nucleotide of one oligonucleotide probe is 8-oxo-dG and the variable position nucleotide of the other oligonucleotide probe is dP.

9. The method of claim 8, wherein dP hybridizes to either A or G, and 8-oxo-dG hybridizes to either A or C.

10. The method of claim of claim 9, wherein hybridization of neither probe indicates a T or U at the position of interest in the target nucleic acid analyte.

11. A method of determining the identity of an unknown nucleotide at a position of interest on a target nucleic acid analyte wherein four nucleotide identities are possible at the position of interest, comprising:

contacting the target nucleic acid analyte under hybridizing conditions with two non-identical oligonucleotide probes each having a variable position nucleotide, wherein the variable position of each oligonucleotide probe is a nucleotide that will base pair with two of the four possible nucleotides, wherein the nucleotides in each variable position overlap in base pair degeneracy with one of the four possible nucleotides;

wherein the hybridizing conditions are sufficient to permit an oligonucleotide probe to hybridize to the target nucleic acid analyte when the nucleotide occupying the variable position base pairs with the nucleotide occupying the position of interest, and does not permit an oligonucleotide probe to hybridize to the target nucleic acid analyte when the nucleotide occupying the variable position does not base pair with the nucleotide occupying the position of interest; and wherein the identity of the position of interest is determined by comparing the variable positions of any hybridized oligonucleotide probe for complementarity and the variable positions of any nonhybridized oligonucleotide probe for lack of complementarity.

12. The method of claim 11, wherein the nucleotide occupying the variable position of one oligonucleotide probe is dP, and the wherein the nucleotide occupying the variable position of the other oligonucleotide probe is 8-oxo-dG.

13. The method of claim 12, wherein dP hybridizes to either A or G, and 8-oxo-dG hybridizes to either A or C.

14. The method of claim of claim 13, wherein hybridization of neither probe indicates a T or U at the position of interest in the target nucleic acid analyte.

* * * * *